(12) United States Patent
Dang et al.

(10) Patent No.: US 7,658,923 B2
(45) Date of Patent: *Feb. 9, 2010

(54) ANTI-CD26 MONOCLONAL ANTIBODIES AS THERAPY FOR DISEASES ASSOCIATED WITH CELLS EXPRESSING CD26

(75) Inventors: Nam Hoang Dang, Houston, TX (US); Chikao Morimoto, Tokyo (JP); Stuart Schlossman, Newton Centre, MA (US)

(73) Assignees: Board of Regents, The University of Texas System, Austin, TX (US); Dana-Farber Cancer Institute, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/676,164

(22) Filed: Feb. 16, 2007

(65) Prior Publication Data

US 2007/0207143 A1     Sep. 6, 2007

(51) Int. Cl.
    A61K 39/395     (2006.01)
(52) U.S. Cl. .................................................. 424/146.1
(58) Field of Classification Search .................. None
    See application file for complete search history.

(56) References Cited

U.S. PATENT DOCUMENTS

| | | | |
|---|---|---|---|
| 5,120,642 A | 6/1992 | Schlossman et al. | 435/7.24 |
| 6,218,372 B1 | 4/2001 | Nabel et al. | 514/44 |
| 6,573,096 B1 | 6/2003 | Chen | 435/326 |
| 6,951,924 B2 * | 10/2005 | Rosen et al. | 530/387.9 |

FOREIGN PATENT DOCUMENTS

| | | |
|---|---|---|
| JP | 2004-500116 | 1/2004 |
| WO | WO 01/74299 | 10/2001 |
| WO | WO 02/04610 | 1/2002 |
| WO | WO 02/31134 | 4/2002 |

OTHER PUBLICATIONS

Skin Cancer Foundation's definition of melanoma downloaded on Jan. 5, 2009.*
Aldinucci et al., "In vitro and in vivo effects of 2'-deoxycoformycin (Pentostatin) on tumour cells from human gammadelta+ T-cell malignancies," *British Journal of Haematology*, 110:188-196, 2000.
Asada et al., "Expression of dipeptidyl aminopeptidase IV activity in human lung carcinoma," *Histopathol.*, 23:265-270, 1993.
Bauvois et al., "Constitutive expression of CD26/dipeptidylpeptidase IV on peripheral blood B lymphocytes of patients with B chronic lymphocytic leukaemia," *Br. J. Cancer*, 79:1042-1048, 1999.
Carbone et al., "CD26/dipeptidyl peptidase IV expression in human lymphomas is restricted to DC30-positive anaplastic large cell and a subset of T-cell non-Hodgkin's lymphomas," *Human Pathol.*, 25:1360-1365, 1994.
Carbone et al., "The expression of CD26 and CD40 ligand is mutually exclusive in human T-cell non-Hodgkin's lymphomas/leukemias," *Blood*, 86(12):4617-4626, 1995.

Dang et al.,"1F7 (CD26): a marker of thymic maturation involved in the differential regulation of the CD3 and CD2 pathways of human thymocyte activation," *J. Immunol.*, 147:2825-2832, 1991.
Dang et al., "Cell surface modulation of CD26 by aniti-1F7 monoclonal antibody," *J. Immunol.*, 145:3963-3971, 1990.
Dang et al., "Comitogenic effect of solid-phase immobilized anti-1F7 on human CD4 T cell activation via CD3 and CD2 pathways," *J. Immunol.*, 144:4092-4100, 1990.
Dang et al., "FcR-mediated crosslinking of Tal (CDw26) induces human T lymphocyte activation," *Cell. Immunol.*, 125:42-57, 1990.
Dang et al., "Human CD4 helper T cell activation: functional involvement of two distinct collagen receptors, 1F7 and VLA integrin family," *J. Exp. Med.*, 172:649-652, 1990.
Datto et al., "Transforming growth factor β induces the cyclin-dependent kinase inhibitor p21 through a p53-independent mechanism," *Proc. Natl. Acad. Sci. USA*, 92:5545-5549, 1995.
De Meester, et al., "Antibody-binding profile of purified and cell-bound CD26—designation of BT5/9 and TA5.9 to the CD26 cluster," *Immunobiology*, 188:145-158, 1993.
Dong et al., "Characterization of adenosine deaminase binding to human CD26 on T cells and its biologic role in immune response," *J. Immunology*, 156:1349-1355, 1996.
Dong et al., "Correlation of the epitopes defined by anti-CD26 mAbs and CD26 function," *Mol. Immunol.*, 35:13-21, 1998.
El-Deiry et al., "WAF1, a potential mediator of p53 tumor suppression," *Cell*, 75:817-825, 1993.
El-Deiry et al., "WAF1/CIP1 is induced in p53-mediated $G_1$ arrest and apoptosis," *Cancer Res.*, 54:1169-1174, 1994.
Fleischer et al., "Molecular associations required for signaling via dipeptidyl peptidase IV (CD26)," *Adv. Exp. Med. Biol.*, 421:117-125, 1997.
Fleischer, "A novel pathway of human T cell activation via a 103 kD T cell activation antigen," *J. Immunol.*, 138:1346-1350, 1987.
Fox et al., "$Ta_1$, a novel 105 KD human T cell activation antigen defined by a monoclonal antibody," *J. Immunol.*, 133:1250-1256, 1984.
Hegen et al., "Cross-linking of CD26 by antibody induces tyorsine phosphorylation and activation of mitogen-activated protein kinase," *Immunology*, 90:257-264, 1997.
Ho et al., "In vitro and in vivo antitumor effect of the anti-CD26 monoclonal antibody 1F7 on human CD30+ anaplastic large cell T-cell lymphoma karpas 299," *Clinical Cancer Res.*, 7:2031-2040, 2001.
Hühn et al., "Molecular analysis of CD26-mediated signal transduction in T cells," *Immunology Letters*, 72:127-132, 2000.
Hühn et al., "The adenosine deaminase-binding region is distinct from major anti-CD26 mAb epitopes on the human dipeptidyl peptidase IV (CD26) molecule," *Cellular Immunology*, 192:33-40, 1999.

(Continued)

*Primary Examiner*—Misook Yu
(74) *Attorney, Agent, or Firm*—Fulbright & Jaworski LLP

(57) ABSTRACT

Therapeutic methods comprising administering anti-CD26 antibodies for the prevention and treatment of cancers and immune diseases associated with expressing CD26 are provided. The invention describes various types of anti-CD26 antibodies and modes of administration.

32 Claims, 12 Drawing Sheets

OTHER PUBLICATIONS

Kähne et al., "Early phosphorylation events induced by DPIV/CD26-specific inhibitors," *Cell. Immunol.*, 189:60-66, 1998.

Kubota et al., "Involvement of dipeptidyl peptidase IV in an in vivo immune response," *Clin. Exp. Immunol.*, 89:192-197, 1992.

Mattern et al., "Antin-CD26 monoclonal antibodies can reversibly arrest human T lymphocytes in the late $G_1$ phase of the cell cycle," *Immunobiol.*, 188:36-50, 1993.

Morimoto and Schlossman, "The structure and function of CD26 in the T-cell immune response," *Immunol. Rev.*, 161:55-70, 1998.

Morimoto et al., "1F7, a novel cell surface molecule, involved in helper function of CD4 cells," *J. Immunol.*, 143:3430-3439, 1989.

Morimotoet al., "The isolation and characterization of the human helper inducer T cell subset," *J Immunol.*, 134: 3762-3769, 1985.

Morrison et al., "A marker for neoplastic progression of human melanocytes is a cell surface ectopeptidase," *J. Exp. Med.*,177:1135-1143, 1993.

Tanaka et al., "CD26 (Dipeptidyl peptidea IV/DPP IV) as a novel molecular marker for differntiated thyroid carcinoma," *Int. J. Cancer*, 64:326-331, 1995.

Tanaka et al., "Cloning and functional expression of the T cell activation antigen CD26," *Journal of Immunology*, 149:481-486, 1992.

Tanaka et al., "The costimulatory activity of the CD26 antigen requires dipeptidyl peptidase IV enzymatic activity," *Proc. Natl. Acad. Sci. USA*, 90:4586-4590, 1993.

Torimoto et al., "Biochemical characterization of CD26 (dipeptidyl peptidae IV): functional comparison of distinct epitopes recognized by various anti-CD26 monoclonal antibodies," *Mol. Immunol.*, 29:183-192, 1992.

Torimoto et al., "Coassociation of CD26 (Dipeptidyl peptidase IV) with CD45 on the surface of human T lymphocytes," *J. Immunol.*, 147:2514-2517, 1991.

Voet et al., In: *Biochemistry*, John Wiley & Sons, pp. 964, 965, 1074 and 1075, 1990.

von Bonin et al., "Dipeptidyl-peptidase IV/CD26 on T cells: analysis of an alternative T-cell activation pathway," *Immunol Rev.*, 161:43-53, 1998.

von Bonin et al., "The T-cell receptor associated $\xi$-chain is required but not sufficient for CD26 (dipeptidylpeptidase IV) mediated signaling," *Immunology Letters*, 55:179-182, 1997.

Waga et al., "The p21 inhibitor of cyclin-dependent kinases controls DNA replication by interaction with PCNA," *Nature*, 369:574-578, 1994.

Wesley et al., "A role for dipeptidyl peptidase IV in suppressing the malignant phenotype of melanocytic cells," *J. Exp. Med.*, 190:311-322, 1999.

Yang and Kornbluth, "All aboard the cyclin train: subcellular trafficking of cyclins and their CDK partners," *Trends Cell Biol.*, 9:207-210, 1999.

Office Action, issued in Japanese Application 2002-589043, dated Jul. 11, 2008 (English Translation).

Gaetaniello et al., "Occupancy of dipeptidyl peptidase IV activates an associated tyrosine kinase and triggers an apoptotic signal in human hepatocarcinoma cells," *Hepatology*, 4:934-942, 1998.

Supplemental Search Report, issued in European Application No. 02769684.8-2402, mail date Jul. 3, 2009.

Cheng et al., "Lung endothelial dipeptidyl peptidase IV promotes adhesion and metastasis of rat breast cancer cells via tumor cell surface-associated fibronectin," *J. Biol. Chem.*, 273:24207-24215, 1998.

Gonzalez-Gronow et al., "Interaction of plasminogen with dipeptidyl peptidase IV initiates a signal transduction mechanism which regulates expression of matrix metalloproteinase-9 by prostate cancer cells," *Biochem. J.*, 355:397-407, 2001.

Waldman et al., "p21 is necessary for the p53-mediated $G_1$ arrest in human cancer cells," *Cancer Research*, 55:5187-5190, 1995.

Xiong et al., "p21 is a universal inhibitor of cyclin kinases," *Nature*, 366:701-704, 1993.

Canadian Office Action issued in International Application No. 2,446,806, dated Sep. 30, 2009.

Iwata and Morimoto, "CD26/dipeptidyl peptidase IV in context: the different roles of a multifunctional ectoenzyme in malignant transformation," *J. Exp. Med.*, 190:301-305, 1999.

* cited by examiner

ANTI-CD26 MONOCLONAL ANTIBODIES AS THERAPY FOR DISEASES ASSOCIATED WITH CELLS EXPRESSING CD26

The present application claim priority to U.S. patent application Ser. No. 10/143,553, filed May 10, 2002, which in turn claims the benefit of U.S. Provisional Application Serial No. 60/290,531, filed May 11, 2001, each of which is hereby incorporated by reference in its entirety without disclaimer.

BACKGROUND OF THE INVENTION

1. Field of the Invention

The present invention relates generally to the fields of cancer, immunology and immunotherapy. More particularly, it concerns the therapeutic use of anti-CD26 antibodies, including monoclonal, humanized, and polyclonal anti-CD26 antibodies, for the prevention and treatment of cancers and immune diseases. Various modes of administration, and doses are described.

2. Description of Related Art

Cancer has become one of the leading causes of death in the western world, second only behind heart disease. Current estimates project that one person in three in the U.S. will develop cancer, and that one person in five will die from cancer. Currently, there are few effective options for the treatment of cancer. The most conventional options of cancer treatment are surgery, radiation therapy and chemotherapy. Typically, surgical methods are used for the diagnosis (by surgical biopsy) and treatment of cancer (surgery to remove cancerous growths). However, if the cancer has metastasized and is widespread, surgery is unlikely to result in a cure and an alternate approach must be taken. Radiation therapy and chemotherapy are other forms of cancer treatments. However, both radiation therapy and chemotherapy being systemic therapies are associated with numerous side effects since normal cells are also affected. Side effects of the currently used cancer therapies include skin irritation, difficulty swallowing, dry mouth, nausea, diarrhea, hair loss, mouth sores, fatigue, bleeding to name a few. Thus, major challenges remain to be overcome for cancer therapy.

Target-directed therapies, such as those using specific antibodies as therapeutic agents, offers advantages over the non-targeted therapies such as systemic chemotherapy via oral or intravenous administration of drugs or radiation therapy. There are two types of antibody-based therapies. The more common type is to identify a tumor antigen (i.e., a protein expressed on tumors and cancer cells and not in normal tissues) and develop an antibody, preferably a monoclonal antibody (mAb) directed to the tumor antigen. One can then conjugate any therapeutic agent, such as a chemotherapeutic agent, a radionuclide, modified toxin, etc., to this antibody to achieve targeted therapy by the therapeutic agent to the tumor. The other kind of antibody based therapy is by providing an antibody which in itself has therapeutic properties against the tumor/cancer cells it targets. The added advantage of this second form of antibody-based therapy is that one may additionally conjugate another therapeutic agent to the therapeutic antibody to achieve a more effective treatment.

The major advantage with any antibody-directed therapy, and of therapy using monoclonal antibodies (mAbs) in particular, is the ability to deliver increased doses of a therapeutic agent to a tumor, with greater sparing of normal tissue from the side effects of the therapeutic agent. Despite the identification of several antibodies for cancer therapies, there is still a need to identify new and more effective therapeutic antibodies to provide therapy for various cancer types.

A membrane protein, CD26, associated with numerous immune-related functions, is known to be expressed on the surface of several human cancers, particularly cancers that are in advanced stages and hence, associated with poor patient prognosis. For example, lung adenocarcinomas are positive for the enzymatic activity of CD26 while other histological types of lung carcinomas are negative for CD26 activity (Asada et al., 1993); CD26 expression is high in differentiated thyroid carcinomas and absent in benign thyroid diseases (Tanaka et al., 1995); high levels of CD26 protein and mRNA expression are found in B-chronic lymphocytic leukemia cells (Bauvois et al., 1999); and CD26 expression is high in aggressive T-cell malignancies, such as T-cell lymphoblastic lymphomas/acute lymphoblastic leukemias (LBL/ALL), T-cell CD30+ anaplastic large cell lymphomas. These cancer types are difficult to treat as they are particularly resistant to current treatment modalities. There is a great need to find therapies that would be useful in treating and preventing such aggressive diseases.

SUMMARY OF THE INVENTION

The present invention overcomes the defects in the art by identifying growth inhibitory properties of anti-CD26 antibodies. The invention therefore provides methods for cancer therapy, where the cancers express a CD26 protein on their surface, using a therapeutic anti-CD26 antibody composition. The anti-CD26 antibody-based therapies of the present invention include the use of unconjugated antibodies including polyclonal antibodies, monoclonal antibodies (mAbs), antibody fragments, humanized mAbs, naked antibodies. The use of conjugated antibodies, where the antibody is conjugated to drugs, other targeted antibody, toxins, enzyme inhibitors, radionuclides, neutron-capturing agents, such as boron addends, chemicals, and other biological agents, is also provided.

Therefore, in some embodiments, the invention provides methods of treating a patient having a cancer that expresses CD26 which comprise administering to the patient, a pharmaceutical formulation comprising an anti-CD26 antibody, where the anti-CD26 antibody binds CD26 and arrests cell cycle which inhibits cell growth.

Various cancers and tumors are contemplated treatable by methods of this invention and include, but are not limited to, T-cell cancers, B-cell cancers, hematological cancers, thyroid cancers, T-cell lymphoma, lung adenocarcinoma, thyroid carcinoma, melanoma, B-cell lymphoma, breast cancers, an ovarian cancers, pancreatic cancers, prostate cancers, colon cancers, bladder cancers, lung cancers, liver cancers, stomach cancers, testicular cancers, uterine cancers, brain cancers, lymphatic cancers, skin cancers, bone cancers, rectal cancers, or sarcomas.

In more specific embodiments, the T-cell cancer may be a T-cell lymphoma such as, a lymphoblastic lymphoma, an acute lymphoblastic leukemia, a T-cell CD30+ anaplastic large cell lymphoma, a peripheral T-cell lymphoma, a T-cell chronic lymphocytic leukemia, an angioimmunoblastic T-cell lymphoma, an angiocentric T-cell lymphoma, a HTLV-related T-cell leukemia, or an adult T-cell leukemia. In other specific embodiments, the B-cell cancer may be a B-cell chronic lymphocytic leukemia, or a B-cell lymphoma.

The invention also contemplates combination therapies, where two or more treatment regimens are applied concurrently to improve the efficacy of the therapy. Thus, in addition to treatment with an anti-CD26 antibody, a patient can be treated with a second therapeutic agent, wherein the second agent is a therapeutic polypeptide, a nucleic acid encoding a therapeutic polypeptide, a chemotherapeutic agent, an immunotherapeutic agent, a cytokine, a chemokine, an activating agent, a radiotherapeutic agent, or a biological response modifier.

The second therapeutic agent may be administered simultaneously with the anti-CD26 antibody. Alternatively, the second agent may be administered at a different time than the anti-CD26 antibody. Thus, the second agent may be administered prior to or after the anti-CD26 antibody treatment.

Several routes for administration of the anti-CD26 antibody are contemplated and include among others, intravenous, intra-arterial, intraperitoneal, intradermal, intratumoral, intramuscular, subcutaneous, intrathecal, intraarthricular, oral, dermal, nasal, buccal, rectal, or vaginal administration.

It is contemplated that the antiCD26 antibody, administered at a dosage range of 1 µg/kg to 1 g/kg will be useful for therapy. Thus it is contemplated that one may use, ranges from 1 µg/kg to 5 µg/kg, or 5 µg/kg to 10 µg/kg, 10 µg/kg to 20 µg/kg, 20 µg/kg to 30 µg/kg, 30 µg/kg to 40 µg/kg, 40 µg/kg to 50 µg/kg, 50 µg/kg to 60 µg/kg, 70 µg/kg to 80 µg/kg, 90 µg/kg to 100 µg/kg, 100 µg/kg to 200 µg/kg, 200 µg/kg to 300 µg/kg, 300 µg/kg to 400 µg/kg, 400 µg/kg to 500 µg/kg, 500 µg/kg to 600 µg/kg, 600 µg/kg to 700 µg/kg, 700 µg/kg to 800 µg/kg, 900 µg/kg to 1 mg/kg, 1 mg/kg to 10 mg/kg, 10 mg/kg to 20 mg/kg, 20 mg/kg to 30 mg/kg, 30 mg/kg to 40 mg/kg, 40 mg/kg to 50 mg/kg, 50 mg/kg to 60 mg/kg, 70 mg/kg to 80 mg/kg, 90 mg/kg to 100 mg/kg, 100 mg/kg to 200 mg/kg, 200 mg/kg to 300 mg/kg, 300 mg/kg to 400 mg/kg, 400 mg/kg to 500 mg/kg, 500 mg/kg to 600 mg/kg, 600 mg/kg to 700 mg/kg, 700 mg/kg to 800 mg/kg, or 900 mg/kg to 1 g/kg are contemplated. Intermediate ranges are also contemplated, for example one may use 1 µg/kg, or 2 µg/kg, or 3 µg/kg, or 4 µg/kg or 5 µg/kg and so on. It will be understood that the exact method of administration and dosages of administration will be decided and adjusted at the time of therapy, depending on the individual needs of a patient, taking into consideration factors such as, age, disease, gender, performance status, etc., and such adjustments will be made by a trained physician. Therefore, the invention is in no way limited by the doses set forth.

In some embodiments, the anti-CD26 antibody maybe a monoclonal antibody. In specific embodiments, the anti-CD26 monoclonal antibody is the 1F7 monoclonal antibody secreted from hybridoma HB 10297 deposited at the American Type Culture Collection (ATCC). This 1F7 antibody and the methods of making it are described in detail in U.S. Pat. No. 5,120,642, incorporated herein by reference.

In other specific embodiments, the anti-CD26 monoclonal antibody is the 5F8 monoclonal antibody. Some other mAb's contemplated as useful include, but are not limited to, 10F8A, 12E3B, 14D10, 2F9, 4G8, 11H9, 18H3A, 9C11, and/or 16D4B. However, any other monoclonal antibody, specific to any epitope of a CD26 protein is contemplated as useful in context of this invention and the present invention is not limited to the above mentioned examples. Additionally, the monoclonal antibody can be administered as a fragment or may be humanized to decrease immunogenicity to human patients.

In yet other embodiments, the invention contemplates the use of a polyclonal anti-CD26 antibodies.

The antibodies of the invention may be prepared against a naturally occurring CD26 protein/polypeptide/peptide, a purified CD26 protein/polypeptide/peptide, a partially purified CD26 protein/polypeptide/peptide, a recombinantly produced CD26 protein/polypeptide/peptide, or a CD26 fusion protein/polypeptide/peptide.

In still other embodiments, it is contemplated that the anti-CD26 antibody will further be attached to another agent, such as but not limited to, a chemotherapeutic agent, a radionuclide, an immunotherapeutic agent, a cytokine, a chemokine, an imaging agent, a toxin, a biological agent, an enzyme inhibitor, or a second antibody. In some specific embodiments, the enzyme inhibitor is an adenosine deaminase inhibitor, or a dipeptidyl peptidase IV inhibitor. In other specific embodiments, the chemotherapeutic agent may be cytosine arabinoside, fluorouracil, methotrexate or aminopterin; anthracycline; mitomycin C; vinca alkaloids; demecolcine; etoposide; mithramycin; or alkylating agents such as chlorambucil or melphalan or others described in later sections in this specification.

In still other specific embodiments, the toxin may be a plant-, a fungal- or bacterial-derived toxin, such as an A chain toxin, a ribosome inactivating protein, α-sarcin, aspergillin, restrictocin, a ribonuclease, diphtheria toxin or *pseudomonas* exotoxin, to mention just a few examples. Radionuclides and imaging agents that may be conjugated to anti-CD26 antibodies are described in sections infra. Other specific embodiments contemplate that other biological agents, such as but not limited to, chemokines, cytokines, retinoic acid and its derivatives, interferons, growth factors.

The invention also provides methods for inducing tumor regression comprising administering to a patient in need thereof a composition comprising an anti-CD26 antibody.

Additionally, the invention provides methods for inducing tumor necrosis comprising administering to a patient in need thereof a composition comprising an anti-CD26 antibody.

In some embodiments, the inventors contemplate methods of treating a patient having a cancer comprising, induction of CD26-expression in cells of the cancer, and administering to the patient a pharmaceutical formulation comprising an anti-CD26 antibody, whereby the anti-CD26 antibody binds CD26 and arrests cell cycle, and/or growth inhibition, and/or cell death and/or tumor regression. The induction of CD26 expression on the cell may be achieved by contacting the cell with a biological factor such as but not limited to a cytokine, a chemokine, growth factor, a retinoid, an interferon, an interleukin, a phorbol ester, an agents that can activate the immune system, a chemotherapeutic agent, an antibody, or an antigen. Alternatively, one may induce the expression of CD26 on a cell by contacting the cell with a chemical agent. Methods for inducing the expression of CD26 in cells are known to the skilled artisan.

The invention also provides a method for increasing the expression of p21, in a cell that expresses CD26 comprising contacting the cell with an anti-CD26 antibody. In one embodiment the cell expressing CD26 is a cancer cell. In specific embodiments, the cancer cell may be a hematological cancer cell, a T-cell cancer cell, a B-cell cancer cell, a thyroid cancer cell, a breast cancer cell, an ovarian cancer cell, a pancreatic cancer cell, a prostate cancer cell, a colon cancer cell, a bladder cancer cell, a lung cancer cell, a liver cancer cell, a stomach cancer cell, a testicular cancer cell, an uterine cancer cell, a brain cancer cell, a lymphatic cancer cell, a skin cancer cell, a bone cancer cell, a rectal cancer cell, a sarcoma cell, a T-cell lymphoma cell, a lung adenocarcinoma cell, a thyroid carcinoma cell, a melanoma cell, a B-cell chronic lymphocytic leukemia, or a B-cell lymphoma. The T-cell cancer may be an aggressive T-cell cancer such as a T-cell lymphoma. In other specific embodiments, the T-cell lymphoma maybe a lymphoblastic lymphoma, an acute lymphoblastic leukemia, a T-cell CD30+ anaplastic large cell lymphoma, a peripheral T-cell lymphoma, a T-cell chronic lymphocytic leukemia, an angioimmunoblastic T-cell lymphoma, an angiocentric T-cell lymphoma, an HTLV-related T-cell leukemia, or an adult T-cell leukemia.

In other embodiments, the CD26-expressing cell is a CD26-transfected Jurkat cell line or a human T-cell, such as a human T-cell clone, or activated T-cells or activated T-cell clones. In yet other embodiments, the CD26 expressing cell is an activated immune cell. Such a cell may be a hyperactivated immune cell, such as an activated T-cells, an activated T-cell with a role in the development of autoimmune diseases and diseases involving activated immune system, an activated T-cell recognizing self antigens, an activated T-cell recognizing allografts, an activated T-cell from donors recognizing host tissues, an activated immune cell expressing CD26-recognizing self antigens, allografts, an activated immune cell expressing CD26 with a role in the development of autoimmune diseases and diseases involving activated immune system, an activated immune cell from donors recognizing host tissues, etc.

In some embodiments, the anti-CD26 antibody is a monoclonal antibody. In one specific embodiment, the anti-CD26 monoclonal antibody (mAb) is secreted from hybridoma HB 10297 deposited at the American Type Culture Collection (ATCC). This mAb is also called as the 1F7 antibody. In another specific embodiment, the anti-CD26 monoclonal antibody (mAb) is the 5F8 antibody. Some other mAb's contemplated as useful include, but are not limited to, 10F8A, 12E3B, 14D10, 2F9, 4G8, 11H9, 18H3A, 9C11, 16D4B. The monoclonal antibody may further be humanized to reduce immunogenicity.

In other embodiments, the anti-CD26 antibody is a polyclonal antibody. Yet other embodiments of the invention, contemplate that the anti-CD26 antibody may be further attached/conjugated to another agent, such as, but not limited to, a chemotherapeutic agent, a radionuclide, an immunotherapeutic agent, a cytokine, a chemokine, an imaging agent, a toxin, a biological agent, an enzyme inhibitor, or a second antibody. In specific embodiments, the enzyme inhibitor is an adenosine deaminase inhibitor, or a dipeptidyl peptidase IV inhibitor.

Also provided are methods for inhibiting cell growth comprising contacting a cell expressing CD26 with an anti-CD26 antibody. In some embodiments of this method, the cell expressing CD26 is a cancer cell. In specific embodiments the cancer cell can be a hematological cancer cell, a T-cell cancer cell, a B-cell cancer cell, a thyroid cancer cell, a breast cancer cell, an ovarian cancer cell, a pancreatic cancer cell, a prostate cancer cell, a colon cancer cell, a bladder cancer cell, a lung cancer cell, a liver cancer cell, a stomach cancer cell, a testicular cancer cell, an uterine cancer cell, a brain cancer cell, a lymphatic cancer cell, a skin cancer cell, a bone cancer cell, a rectal cancer cell, or a sarcoma cell. In more specific embodiments, the cancer cell can be a T-cell lymphoma cell, a lung adenocarcinoma cell, a thyroid carcinoma cell, a melanoma cell, a B-cell chronic lymphocytic leukemia, or a B-cell lymphoma.

In yet other specific embodiments, the T-cell cancer can be an a T-cell cancer with poor prognosis and is exemplified, in non-limiting examples, by T-cell lymphomas such as lymphoblastic lymphoma, acute lymphoblastic leukemia, T-cell CD30+ anaplastic large cell lymphoma, peripheral T-cell lymphoma, T-cell chronic lymphocytic leukemia, angioimmunoblastic T-cell lymphoma, angiocentric T-cell lymphoma, HTLV-related T-cell leukemia, and adult T-cell leukemia.

In one aspect of the method, the cell growth inhibited is metastatic cell growth. In other aspects of the method, inhibiting cell growth comprises arresting cell growth.

In yet other embodiments, the CD26 expressing cell is a CD26-transfected Jurkat cell line or a human T-cell, such as a human T-cell clone, or activated T-cells or activated T-cell clones. In yet other embodiments, the CD26 expressing cell is an activated immune cell. Such a cell may be a hyperactivated immune cell, such as an activated T-cell, an activated T-cell with a role in the development of autoimmune diseases and diseases involving activated immune system, an activated T-cell recognizing self antigens, an activated T-cell recognizing allografts, an activated T-cell from donors recognizing host tissues, an activated immune cell expressing CD26 recognizing self antigens, allografts, an activated immune cell expressing CD26 with a role in the development of autoimmune diseases and diseases involving activated immune system, an activated immune cells from donors recognizing host tissues, etc. Thus, the method is contemplated useful in providing therapy for diseases of the immune-system associated with hyperactive immune cells, such as, autoimmune diseases, organ transplantation, graft versus host diseases etc. This includes diseases such as, but not limited to, Addison's disease, alopecia, ankylosing spondylitis, antiphospholipid syndrome, Behcet's disease, chronic fatigue syndrome, Crohn's disease, ulcerative colitis, diabetes, fibromyalgia, Goodpasture syndrome, Graves' disease, idiopathic thrombocytopenic purpura (ITP), lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vasculitis, vitiligo, Wegener's granulomatosis.

The invention also provides a method of inducing apoptosis in a cancer cell expressing CD26, comprising contacting the cell with a composition comprising an anti-CD26 antibody.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Cells were evaluated for CD26, CD3 and CD2 expression by flow cytometry. Percentage of cells expressing the particular surface marker is indicated.

(FIG. 3A) CD26 surface expression prior to tumor injection into SCID mice. 1×10$^6$ tumor cells were injected i.p. in SCID mice, and tumor mass was subsequently harvested following the development of palpable tumors. Single cell suspensions were then created and CD26 surface expression was determined by flow cytometry. (a=negative control, b=CD26) (FIG. 3B) CD26 surface expression on single cell suspensions from tumor mass harvested from SCID mice. 1×10$^6$ tumor cells were injected i.p. in SCID mice, and tumor mass was subsequently harvested following the development of palpable tumors. Single cell suspensions were then created and CD26 surface expression was determined by flow cytometry. (a=negative control, b=CD26).

(FIG. 4A) One day following i.p. inoculation of SCID mice with 1×10$^6$ Karpas 299 cells per mouse, i.p. treatment with saline alone, isotype control Ab (5 μg/injection or 10 μg/injection), 1F7 (5 μg/injection or 10 μg/injection) was then administered every other day for a total of 10 injections. Arm 1: saline alone (n=13); arm 2: isotype control Ab (5 μg/injection, n=10); arm 3: isotype control Ab (10 μg/injection, n=5); arm 4: anti-CD26 mAb 1F7 (10 μg/injection, n=10); arm 5: anti-CD26 mAb 1F7 (5 μg/injection, n=14) (FIG. 4B) One day following i.p. inoculation of SCID mice with 3×10$^6$ Karpas 299 cells per mouse, i.p. treatment with saline alone, isotype control Ab (20 μg/injection) or 1F7 (5 μg/injection, 10 μg/injection or 20 μg/injection) was then administered every other day for a total of 10 injections. Arm 1: saline alone (n=5); arm 2: isotype control Ab (20 μg/injection, n=5); arm 3: 1F7 (5 μg/injection, n=5); arm 4: 1F7 (10 μg/injection, n=5); arm 5: 1F7 (20 μg/injection, n=5).

DESCRIPTION OF ILLUSTRATIVE EMBODIMENTS

Figure 1A:
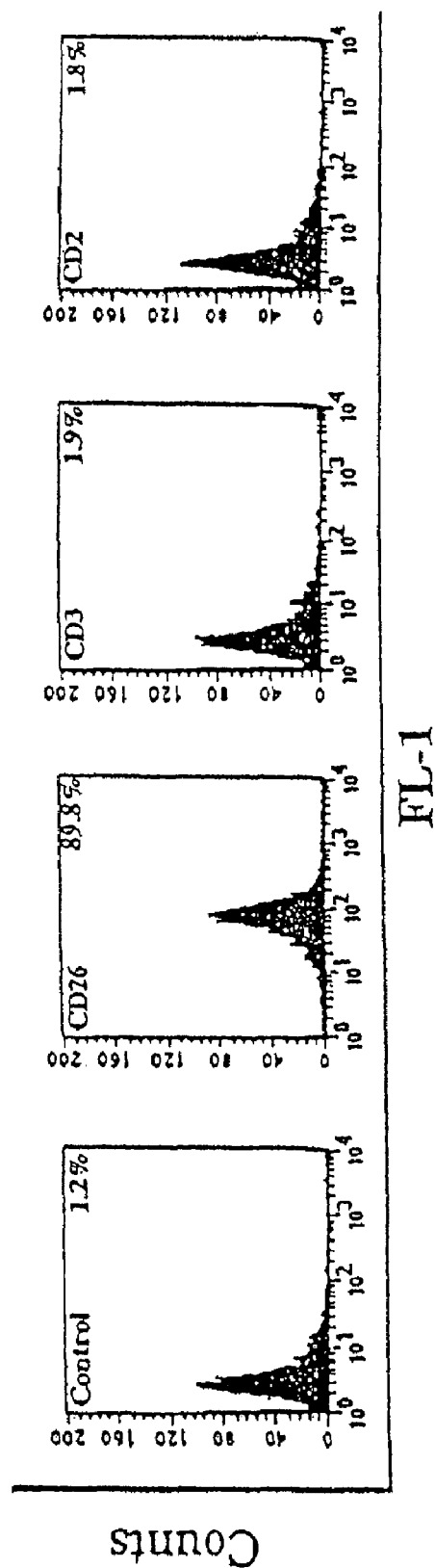
FIGS. 1A. & 1B. Phenotypic characterization of Karpas 299.

The present invention provides therapeutic methods that employ anti-CD26 antibodies for the prevention and treatment of cancers. Binding of a soluble anti-CD26 mAb, such as 1F7, has been shown to inhibit growth of cells, exemplified by Karpas 299 cells, a human CD30+ anaplastic large cell T-cell lymphoma cell line, as well as Jurkat cells both in in vitro and in vivo studies. Anti-CD26 binding results in growth arrest at the G1/S checkpoint, associated with an increased p21 expression (a cell cycle protein) that is dependent on de novo protein synthesis. The upregulation of p21 and cell cycle arrest at the G1/S checkpoint have been shown to be dependent on the enzymatic activity of CD26 (DPPIV), in experiments using cells that express mutated versions of CD-26 that lack enzyme activity.

Furthermore, the inventors have shown, using a SCID mouse tumor model, that treatment with the anti-CD26 antibody leads to significantly enhanced survival of tumor bearing mice. Thus, the present invention provides anticancer therapies which use an anti-CD26 antibody for the treatment of human cancers that express CD26.

The expression of CD26 has been documented in several human cancers, including aggressive T-cell malignancies, which are resistant to current treatment modalities. The present invention, therefore, provides methods of treatment for such cancers using an anti-CD26 antibodies to inhibit tumor growth. Several types of anti-CD26 antibodies are contemplated as useful for treatment regimens and include, polyclonal antibodies, monoclonal antibodies (mAb 1F7; and mAb 5F8 as some non-limiting examples), humanized versions of antibodies as well as antibody conjugates.

Although, the CD26 protein is known to be involved in a variety of functional aspects, the increase in p21 expression in cells, following the binding of the anti-CD26 antibody, shows for the first time a functional association between CD26 and regulators of the cell cycle in cancer.

The present inventors have also demonstrated that binding of a soluble anti-CD26 monoclonal antibody induces a G1/S arrest in CD26-transfected Jurkat cell lines and in human T-cell clones. It is known that CD26 is expressed on a subset of resting CD4+ memory T-cells and that this expression is enhanced upon T-cell activation. In addition, CD26 contributes directly to increased antigen sensitivity of late-stage T-cell clones. Hyperactive immune diseases, such as graft-versus-host disease (GVDH) and autoimmune diseases, involve hyperactivated T-cells. Therefore, in addition to providing effective therapy against cancers that express CD26, the present inventors contemplate therapeutic utility of the anti-CD26 antibodies for the treatment of for hyperactive immune conditions, including autoimmune diseases such as but not limited to Addison's disease, alopecia, ankylosing spondylitis, antiphospholipid syndrome, Behcet's disease, chronic fatigue syndrome, Crohn's disease, ulcerative colitis, diabetes, fibromyalgia, Goodpasture syndrome, Graves' disease, idiopathic thrombocytopenic purpura (ITP), lupus, Meniere's multiple sclerosis, myasthenia gravis, pemphigus vulgaris, primary biliary cirrhosis, psoriasis, rheumatoid arthritis, rheumatic fever, sarcoidosis, scieroderma, vasculitis, vitiligo, Wegener's granulomatosis, etc., organ transplants and graft versus host diseases. Currently, in the U.S. alone, there are an estimated 10-20 million cases of autoimmune diseases diagnosed every year. Therefore, the anti-CD26 antibody treatments for immune related diseases is an important development.

A. CD26 and Anti-CD26 Anibodies

CD26 is a 110-kd surface glycoprotein with an array of diverse functional properties that is expressed on a number of tissues, including epithelial cells and leukocyte subsets (Morimoto and Schlossman, 1998; von Bonin et al., 1998). The CD26 protein is a membrane-associated ectopeptidase that possesses dipeptidyl peptidase IV (DPPIV) activity in its extracellular domain and is able to cleave amino-terminal dipeptides from polypeptides with either L-proline or L-alanine at the penultimate position.

Work over the past decade has shown CD26 to be a molecule with a plethora of functions in basic human T-cell physiology. For example, CD26 cleaves certain chemokines involved in T-cell and monocyte function (Oravecz et al., 1997; Proost et al., 1998). Other studies have identified CD26 as the adenosine deaminase (ADA) binding protein which regulates ADA surface expression. It is believed that the CD26/ADA complex plays a key role in the catalytic removal of local adenosine to regulate immune system function (Dang et al., 1996; Kameoka et al., 1993; Morrison et al., 1993).

Although constitutively expressed in the liver, intestine and kidney, CD26 expression level is tightly regulated on T-cells, and its density is markedly enhanced after T-cell activation. In resting T-cells, CD26 is expressed on a subset of CD4+ memory T-cells, and this CD4+ CD26 high T-cell population has been shown to respond maximally to recall antigens. In fact, CD26 itself is involved in the signal transducing process of T-cells under certain experimental conditions. Cross-linking of CD26 and CD3 with immobilized monoclonal antibodies (mAbs) can induce T-cell activation and IL-2 production. Moreover, anti-CD26 antibody treatment of T-cells leads to a decrease in the surface expression of CD26 via its internalization, and this antibody-induced modulation of CD26 on T-cells results in an enhanced proliferative response to anti-CD3 or anti-CD2 stimulation. While ligation of the CD26 molecule by anti-CD26 mAb, 1F7, induces increased tyrosine phosphorylation of signaling molecules such as CD3zeta and p56lck, soluble anti-CD26 mAbs and DPPIV inhibitors suppress T-cell growth and function in certain instances.

In addition, activation of T-cell by various stimuli increases CD26 surface expression and thus, CD26 is used as a T-cell activation marker (Fox et al., 1984; Morimoto et al., 1989). CD26 is also a co-stimulatory surface molecule involved in the CD3 and CD2 pathways of T-cell activation.

Besides its involvement in immunoregulation, it was believed that CD26 may have a role in the development of certain human tumors. Most lung adenocarcinomas are DPPIV-positive, while other histological types of lung carcinoma are DPPIV-negative (Asada et al., 1993). In addition, CD26 expression is high in differentiated thyroid carcinomas but is absent in benign thyroid diseases (Tanaka et al., 1995). It also appears to have a role in melanoma development as its expression is lost with malignant transformation of melanocytes (Morrison et al., 1993; Wesley et al., 1999). High levels of CD26 protein expression and mRNA transcripts are found in B-chronic lymphocytic leukemia cells and activated B-cells, as compared to normal resting B-cells (Bauvois et al., 1999). Meanwhile, CD26 expression on T-cell malignancies appears to be restricted to aggressive pathologic entities such as T-cell lymphoblastic lymphomas/acute lymphoblastic leukemias (LBL/ALL) and T-cell CD30+ anaplastic large cell lymphomas, being detected only on a small percentage of indolent diseases such as mycosis fungoides. Significantly, within the T-cell LBL/ALL subset, CD26 expression is an independent marker of poor prognosis patients (Carbone et al., 1995; Carbone et al., 1994).

Numerous antibodies against CD26 have been generated and described including the monoclonal antibodies such as 1F7, Ta1, 5F8, 10F8A, 12E3B, 14D10, 2F9, 4G8, 11H9, 18H3A, 9C11, 16D4B, TA5.9, developed by standard hybridoma techniques (Morimoto et al., 1989; Torimoto et al., 1992; U.S. Pat. No. 5,120,642; DeMeester et al., 1994; Dong et al., 1998, all incorporated herein by reference).

Corresponding to the diverse role of CD26, CD26 antibodies mediate pleomorphic cellular functions. For example, when crosslinked with specific mAbs, CD26 is capable of activating an alternate pathway of T-cell activation, possibly due to its physical association with CD45, a transmembrane protein tyrosine phosphatase (Dang et al., 1990a; Dang et al., 1990b; Dang et al., 1990c; Dang et al., 1991; Fleischer, 1987; Hegen et al., 1997; Dang et al., 1990d; Torimoto et al., 1991). Yet other studies have shown that soluble anti-CD26 mAbs and DPPIV inhibitors suppress T-cell growth and function in certain instances (Dang et al.; 1996; Kahne et al., 1998; Kubota et al., 1992; Mattern et al., 1993). These studies, and others described supra, suggest that CD26 may have a potential role in the development of certain neoplasms, including aggressive T-cell hematologic malignancies (Carbone et al., 1995; Carbone et al.; 1994), besides being an immunoregulatory molecule.

Dong and co-workers, divided 13 anti-CD26 antibodies into 5 different epitope groups located between the 1-247, 248-358, 359-449, 450-577 and 359-653 amino acid residues of the CD26 protein based on deletion analysis of CD26 deletion mutants, immunoblotting and direct binding assays. In that study, Dong et al. (1998), incorporated herein by reference, have shown that distinct epitopes specific to different anti-CD26 mAbs are associated with different functional domains of CD26. For example, while the mAbs against two of these groups, the 248-358 and the 359-449 amino acid regions, induced the modulation of CD26 and had a co-stimulatory effect on T-cell proliferation, only one of these antibodies against the 359-449 amino acid region was also associated with ADA binding. This accounts for some different functional effects shown by different anti-CD26 antibodies.

Thus, CD26 and its antibodies are complex molecules with a diverse range of functions. The present invention demonstrates unequivocally that CD26 has a significant role in tumor development and that antibodies to CD26 cause growth arrest and growth inhibition in cancer cells bearing CD26 on the surface.

In addition, while previous reports showed that CD26 ability to mediate activation signals is dependent on a functional CD3/TcR complex (von Bonin et al., 1998; Dang et al., 1990d), the present inventors show that CD26 can transmit signals resulting in alterations of T-cell biological responses in the absence of a functional CD3/TcR complex. In normal T-cells, engagement of CD26 results in an increased phosphorylation of proteins involved in T-cell signal transduction, mediated in part through the physical association of CD26 and CD45 (Hegen et al., 1997; Torimoto et al., 1991). The inventors are currently investigating the mechanism involved in CD26 engagement leading to cell cycle. Although, G1 arrest following enforced CD26 expression was observed in melanoma cells (Wesley et al., 1999), the present inventors have demonstrated the functional association between CD26-mediated G1/S arrest and altered p21 expression.

B. p21

In eukaryotic cells, cell cycle progression is controlled at the G1/S checkpoint by a group of related enzymes known as the cyclin-dependent kinases (CDKs), which are positively regulated by their physical association with regulatory subunits called cyclins (Yang and Kornbluth, 1999). However, enzymatic activities of the CDK-cyclin complexes are negatively regulated by a set of proteins termed CDK inhibitors. One of these CDK inhibitors is p21 (also called WAF1, Cip1, SDI1) which blocks multiple cyclin-CDK complexes through its physical association with these structures (El-Deiry et al., 1993; Xiong et al., 1993). In addition, through its direct interaction with proliferating cell nuclear antigen (PCNA), p21 can inhibit DNA replication (Waga et al., 1994). Various stimuli can induce p21 expression, including cellular damage, serum factors, and phorbol esters, and p21 induction has been shown to be both p53-dependent and p53-independent, depending on the stimuli (El-Diery et al.; 1993; El-Diery et al.; 1994; Datto et al., 1995).

As a downstream target of the p53 tumor suppressor gene, p21 has been implicated indirectly in malignant transformation. Induction of p53 in response to DNA damage results in G1 checkpoint arrest, at which point DNA repair is accomplished prior to DNA replication in S phase. Consistent with its presumed role as a downstream effector for p53, p21 has been shown to inhibit proliferating cell nuclear antigen (PCNA) dependent DNA replication but not DNA repair in vitro.

U.S. Pat. No. 6,218,372, incorporated herein by reference, describes the role of p21 in tumor formation and its ability to reverse malignant phenotypes in vivo. p21 expression is sufficient to produce tumor and restenosis suppressor effects and p21 expression facilitates transcriptional activation by NF-κB which influences the expression of genes, such as adhesion molecules, associated with cell differentiation.

The present invention demonstrates that the administration of anti-CD26 antibodies results in cell growth inhibition and a corresponding increase in the expression of p21.

C. Role in Immune Diseases

While CD26 function in immune regulation has been well-studied, its role in the clinical setting is not yet clearly defined, although available data suggest that it may be involved in the development of certain human diseases. Consistent with the findings that CD26 is a marker of T-cell-activation and has a functional role in this process, CD26 may have a role in certain autoimmune diseases as a regulator of T-cell activation and lymphokine synthesis, including rheumatoid arthritis, Graves' disease, and multiple sclerosis (Hafler et al., 1985; Mizokami et al., 1996; Eguchi et al., 1989; Gerli et al., 1996). Circulating T lymphocytes from patients with these autoimmune diseases express high level of CD26 surface expression and in several instances, the level of expressed CD26 correlates with disease activity (Hafler et al., 1985; Mizokami et al., 1996; Eguchi et al., 1989; Gerli et al., 1996). Furthermore, in patients with rheumatoid arthritis, antibody-induced modulation of CD26 expression results in enhanced IL-2 and gamma-IFN synthesis in peripheral blood T-cells, and a decreased gamma-IFN production while having no effect on IL-2 production in synovial fluid T-cells (Gerli et al., 1996). In addition, inhibition of CD26/DPPIV enzymatic activity in vivo prolongs cardiac allograft survival in rat recipients, suggesting a role for CD26 in alloantigen-mediated immune regulation in vivo and in the mechanism of allograft rejection (Korom et al., 1997).

Previous work has shown that treatment with anti-CD26 monoclonal antibody at effective doses is well-tolerated in patients without inducing severe toxicity. In a pilot study, Bacigalupo et al. (1985) treated 8 patients with severe refractory graft-versus-host-disease with a murine anti-CD26 monoclonal antibody recognizing human CD26 (De Meester et al., 1993). Along with a decrease in the number of circulating CD26+ T-cells, there was a significant improvement in the severity of the disease. There were 2 complete responders and 2 partial responders, with 5 of 8 patients surviving at least 1 year post treatment. Importantly, treatment with anti-CD26 monoclonal antibody was well-tolerated with acceptable immediate adverse reactions, suggesting that future therapies involving anti-CD26 monoclonal antibody can be administered with tolerable side effects.

The present inventors have demonstrated that binding of a soluble anti-CD26 monoclonal antibody, such as 1F7, can induce G1/S arrest in cells such as CD26-transfected Jurkat cell lines as well as human T-cell clones. Thus, the present inventors envision that anti-CD26 antibody treatments will be of therapeutic use in clinical setting involving activated immune system disorders, including autoimmune diseases, graft-versus-host disease, and organ transplants, where one can induce cell cycle arrest in hyperactivated immune cells.

It is envisioned that, anti-CD26 antibodies will be used in conjunction with other treatment modalities in graft versus host diseases to treat the disease. Additionally, patients with different stages or clinical severity of graft versus host diseases can be selected for treatment with a anti-CD26 therapy. In such therapies it is further envisioned that while in some embodiments, one may employ an anti-CD26 antibody alone, in other embodiments one will employ an anti-CD26 antibody that has been suitably modified, such as being conjugated to agents targeting specific activated T-cells or other immune cells responsible for graft versus host diseases, to treat the disease. The agents that may be conjugated with an anti-CD26 antibody to treat the disease include, but not are limited to, other specific antibody, growth factors, chemokine, cytokine, toxins, or agents that recognize specific targets on these effector cells. Besides conjugation, an anti-CD26 mAb can be used in combination with agents targeting the effector cells responsible for the disease. Anti-CD26 antibody can also be used in these diseases in combination with other pharmaceutical/clinical agents such as selected antibiotics/antifungal/antiviral agents to minimize potential infections arising from the diseases or from the anti-CD26 treatment regimen. In addition, the specific epitopes recognized by anti-CD26 monoclonal antibodies have been shown to have differential effects in CD26-signaling, and binding. Thus, the inventors contemplate that different anti-CD26 mAb recognizing distinct epitopes may lead to different efficacy and toxicity profiles.

D. Antibodies a. Antibody Generation

The present invention provides therapeutic uses for anti-CD26 antibodies. Although, in some embodiments, the invention describes the 1F7 and the 5F8 monoclonal antibodies, other monoclonal antibodies as well as polyclonal antibodies against the CD26 antigen may be used effectively in the preventive and therapeutic methods provided by the present invention. Thus, the present invention is not limited to any specific anti-CD26 antibody/antibodies and it is contemplated that any antibody specific for a CD26 protein, polypeptide or peptide may be used. The invention also contemplates the use of a biologically functional equivalent of an anti-CD26 antibody. The term "CD26 protein/peptide/polypeptide" or "CD26 antigen" is used herein to refer to a CD26 protein, polypeptide or peptide, irrespective of whether the it occurs naturally, is purified, is partially purified, or is produced by recombinant DNA methods, fusion-protein methods, protein synthesis methods, etc., or is a biological functional equivalent thereof.

A biologically functional equivalent is molecule where modifications and/or changes may be made in the structure of the polynucleotides and/or proteins encoding the molecule, while obtaining molecules having similar or improved characteristics. In context of this invention the molecule may be either a CD26 antigen or a CD26 antibody. The biological functional equivalent may comprise a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. Methods for preparing such equivalents are well known in the art.

Means for preparing and characterizing antibodies are well known in the art (See, e.g., Antibodies: A Laboratory Manual, Cold Spring Harbor Laboratory, 1988; incorporated herein by reference).

This section presents a brief discussion on the methods for generating antibodies.

(i) Polyclonal Antibodies

Briefly, a polyclonal antibody is prepared by immunizing an animal with an immunogenic composition (comprising a CD26 antigen in this case) in accordance with the present invention and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other proteins such as ovalbumin, mouse serum albumin, rabbit serum albumin, bovine thyroglobulin, or soybean trypsin inhibitor can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. Other bifunctional or derivatizing agent may also be used for linking, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs.

For production of rabbit polyclonal antibodies, the animal can be bled through an ear vein or alternatively by cardiac puncture. The procured blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix or protein A followed by antigen (peptide) affinity column for purification.

(ii) Monoclonal Antibodies

A "monoclonal antibody" refers to homogenous populations of immunoglobulins which are capable of specifically binding to a CD26 protein. It is understood that the CD26 protein may have one or more antigenic determinants. The antibodies of the invention may be directed against one or more of these determinants.

Monoclonal antibodies (mAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified CD26 antigen protein, polypeptide or peptide. The immunizing composition is administered in a manner effective to stimulate antibody producing cells.

The methods for generating mAbs generally begin along the same lines as those for preparing polyclonal antibodies. Rodents such as mice and rats are preferred animals, however, the use of rabbit, sheep, goat, monkey cells also is possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B-cells), are selected for use in the mAb generating protocol. These cells may be obtained from biopsied spleens or lymph nodes. Spleen cells and lymph node cells are preferred, the former because they are a rich source of antibody-producing cells that are in the dividing plasmablast stage.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant-cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (hypoxanthine-aminopterin-thymidine (HAT) medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific mAb produced by the fused cell hybrid. The body fluids of the animal, such as serum or ascites fluid, can then be tapped to provide mAbs in high concentration.

The individual cell lines could also be cultured in vitro, where the mAbs are naturally secreted into the culture medium from which they can be readily obtained in high concentrations.

mAbs produced by either means may be further purified, if desired, using filtration, centrifugation and various chromatographic methods such as HPLC or affinity chromatography. Fragments of the mAbs of the invention can be obtained from the purified mAbs by methods which include digestion with enzymes, such as pepsin or papain, and/or by cleavage of disulfide bonds by chemical reduction. Alternatively, mAb fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Antibodies to CD26 antigen have already been generated using such standard techniques. For example, U.S. Pat. No. 5,120,642, incorporated herein by reference, describes the generation of the 1F7 mAb, and its characterization. Developed to aid the distinction between helper-inducer and suppressor-inducer cells in a CD4+ lymphocyte population, mAb 1F7 was produced from a hybrid cell line developed from immunization of Balb/c J mice with a stimulated T-cell line derived from the new world primate species *Aotus trivirgatus*. Briefly, Balb/c J mice were immunized with cells of a PHA-stimulated T-cell line derived from the new world primate species *Aotus trivirgatus* using standard hybridoma procedures. The mouse splenocytes were harvested and fused with the myeloma cell line NS-1. The cell population was cultured in HAT medium to obtain hybridoma cells to be cloned. Hybridoma cultures containing antibodies reactive with human T-cells were selected. Cloning and recloning of hybridoma cultures containing mAbs reactive with human T-cells were performed by limiting dilution methods in the presence of feeder cells. Malignant ascites then were developed and used for analysis. The isotype of the mAb was determined to be mouse isotype IgG1 by staining with fluorescein-labeled goat anti-mouse IgG1 and failure to stain with fluorescein-labeled antibodies directed against other subclasses of mouse Ig. A culture of hybridoma cells which produce the anti-1F7 mAb, deposited as of Nov. 21, 1989, with the American Type Culture Collection, 12301 Parklawn Drive, Rockville, Md. 20852, and has been assigned ATCC No. HB 10297.

Other mAbs against CD26 that have been generated, by standard hybridoma techniques, by the present inventors, include, 10F8A, 12E3B, 14D10, 2F9, 4G8, 11H9, 18H3A, 9C11, and 16D4B (Dong et al., 1998, incorporated herein by reference). Yet another anti-CD26 mAb is 5F8 (Morimoto et al., 1989; Torimoto et al., 1992, incorporated herein by reference).

(iii) Humanized Antibodies

Humanized mAbs are antibodies of animal origin that have been modified using genetic engineering techniques to replace constant regions and/or variable region framework sequences with human sequences, while retaining the original antigen specificity. Such antibodies can also include a humanized heavy chain associated with a donor or acceptor unmodified light chain or a chimeric light chain, or vice versa. Such antibodies are commonly derived from rodent antibodies, for example, the murine Ab of the present invention, with specificity against human antigens and are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). "CDRs" are defined as the complementarity determining region amino acid sequences of an antibody. CDRs are contained within the hypervariable regions of immunoglobulin heavy and light chains. CDRs provide the majority of contact residues for the binding of the antibody to the antigen or epitope. CDRs of interest in this invention are derived from donor antibody variable heavy and light chain sequences, and include functional fragments and analogs of the naturally occurring CDRs, which fragments and analogs also share or retain the same antigen binding specificity and/or neutralizing ability as the donor antibody from which they were derived. When combined into an intact antibody, the humanized immunoglobulins are substantially non-immunogenic in humans and retain substantially the same affinity as the donor immunoglobulin to the antigen, such as a protein or other compound containing an epitope.

Generally, a humanized antibody has one or more amino acid residues introduced into it from a source which is non-human. These non-human amino acid residues are often referred to as "import" residues, which are typically taken from an "import" variable domain. A humanized antibody is one in which only the antigen-recognized sites, or complementarity-determining hypervariable regions (CDRs) are of non-human origin, whereas all framework regions (FR) of variable domains are products of human genes.

Humanization can be essentially performed following the method of Winter and co-workers (Jones et al., 1986; Riechmann et al., 1988; Verhoeyen et al., 1988), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some framework region (FR) residues are substituted by residues from analogous sites in rodent antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference. Human antibodies may also be produced by transforming B-cells with EBV and subsequent cloning of secretors as described by Hoon et al., (1993).

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

(iv) Human Antibodies

Human mAbs can be made by the hybridoma method. Human myeloma and mouse-human heteromyeloma cell lines for the production of human mAbs have been described, for example, by Kozbor (1984), and Brodeur et al. (1987).

It is now possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region (Ji) gene in chimeric and germ-line mutant mice results in complete inhibition of endogenous antibody production. Transfer of the human germ-line immunoglobulin gene array in such germ-line mutant mice will result in the production of human antibodies upon antigen challenge (Jakobovits et al., 1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats (Johnson et al., 1993). Several sources of V-gene segments can be used for phage display. Clackson et al. (1991), isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991), or Griffith et al. (1993).

In a natural immune response, antibody genes accumulate mutations at a high rate (somatic hypermutation). Some of the changes introduced will confer higher affinity, and B-cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires has been described by Waterhouse et al. (1993), and the isolation of a high affinity human antibody directly from such large phage library is reported by Griffith et al. (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (PCT patent application WO 93/06213). Unlike traditional humanization of rodent antibodies by CDR grafting, this technique provides completely human antibodies, which have no framework or CDR residues of rodent origin.

(v) Bispecific Antibodies

Bispecific antibodies are monoclonal, preferably human or humanized, antibodies that have binding specificities for at least two different antigens. In the present case, one of the binding specificities is for a CD26 antigen, the other one is for any other antigen, and preferably for another receptor or receptor subunit. For example, bispecific antibodies specifically binding a CD26 antigen are within the scope of the present invention. Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, 1983). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 and Traunecker et al. (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. For further details of generating bispecific antibodies see, for example, Suresh et al. (1986).

(vi) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

b. Cross-Reactive Antibodies and Epitopes

The invention further encompasses other anti-CD26 antibody-based compositions, such as antibody conjugates and immunotoxins, that bind to the same antigens and/or epitopes as the antibodies disclosed herein, i.e., to a CD26 antigen. Such antibodies may be of the polyclonal or monoclonal type, with monoclonals being generally preferred.

The identification of an antibody that binds to a cancer antigen or epitope, such as to CD26 antigen or an epitope thereof, in substantially the same manner as an antibody of the invention is a fairly straightforward matter. This can be readily determined using any one of variety of immunological screening assays in which antibody competition can be assessed.

For example, where the test antibodies to be examined are obtained from different source animals, or are even of a different isotype, a simple competition assay may be employed in which the control and test antibodies are premixed and then applied to an antigen composition. By "antigen composition" is meant any composition that contains a CD26 antigen or related cancer antigen as described herein. Thus, protocols based upon ELISAs and Western blotting are suitable for use in such simple competition studies.

In such embodiments, one would pre-mix the control antibodies with varying amounts of the test antibodies (e.g., 1:1, 1:10 and 1:100) for a period of time prior to applying to an antigen composition, such as an antigen-coated well of an ELISA plate or an antigen adsorbed to a membrane (as in dot blots and Western blots). By using species or isotype secondary antibodies one will be able to detect only the bound control antibodies, the binding of which will be reduced by the presence of a test antibody that recognizes the same epitope/antigen.

In conducting an antibody competition study between a control antibody, such as an anti-CD26 antibody, and any test antibody, one may first label the control with a detectable label, such as, e.g., biotin or an enzymatic, radioactive or fluorescent label, to enable subsequent identification. In these cases, one would incubate the labeled control antibodies with the test antibodies to be examined at various ratios (e.g., 1:1, 1:10 and 1:100) and, after a suitable period of time, one would then assay the reactivity of the labeled control antibodies and compare this with a control value in which no potentially competing test antibody was included in the incubation.

The assay may again be any one of a range of immunological assays based upon antibody hybridization, and the control antibodies would be detected by means of detecting their label, e.g., using streptavidin in the case of biotinylated antibodies or by using a chromogenic substrate in connection with an enzymatic label or by simply detecting a radioactive or fluorescent label. An antibody that binds to substantially the same epitope as the control antibodies will be able to effectively compete for binding and thus will significantly reduce control antibody binding, as evidenced by a reduction in bound label.

The reactivity of the labeled control antibodies in the absence of any test antibody would be the control high value. The control low value would be obtained by incubating the labeled antibodies with unlabelled antibodies of the same type, when competition would occur and reduce binding of the labeled antibodies. A significant reduction in labeled antibody reactivity in the presence of a test antibody is indicative of a test antibody that recognizes the same epitope, i.e., one that "cross-reacts" with the labeled antibody. A significant reduction is a reproducible, i.e., consistently observed, reduction in binding.

c. Antibody Conjugates

Antibody conjugates comprising a CD26 antibody linked to another agent, such as but not limited to a therapeutic agent, a detectable label, a cytotoxic agent, a chemical, a toxic, an enzyme inhibitor, a pharmaceutical agent, etc. form further aspects of the invention. Diagnostic antibody conjugates may be used both in in vitro diagnostics, as in a variety of immunoassays, and in in vivo diagnostics, such as in imaging technology.

Certain antibody conjugates include those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Other antibody conjugates, intended for functional utility, include those where the antibody is conjugated to an enzyme inhibitor such as an adenosine deaminase inhibitor, or a dipeptidyl peptidase IV inhibitor.

(i) Radiolabeled Antibody Conjugates.

In using an antibody-based molecule as an in vivo diagnostic agent to provide an image of, for example, brain, thyroid, breast, gastric, colon, pancreas, renal, ovarian, lung, prostate, hepatic, and lung cancer or respective metastases, magnetic resonance imaging, X-ray imaging, computerized emission tomography and such technologies may be employed. In the antibody-imaging constructs of the invention, the antibody portion used will generally bind to the cancer marker, such as CD26 antigen, and the imaging agent will be an agent detectable upon imaging, such as a paramagnetic, radioactive or fluorescent agent.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). MAbs also may be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled mAbs of the present invention may be produced according to well-known methods in the art. For instance, mAbs can be iodinated by contact with sodium or potassium iodide and a chemical oxidizing agent such as sodium hypochlorite, or an enzymatic oxidizing agent, such as lactoperoxidase. MAbs according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA).

Fluorescent labels include rhodamine, fluorescein isothiocyanate and renographin.

(ii) Immunotoxins

The invention further provides immunotoxins in which an antibody that binds to a cancer marker, such as CD26 antigen, is linked to a cytotoxic agent. Immunotoxin technology is fairly well-advanced and known to those of skill in the art. Immunotoxins are agents in which the antibody component is linked to another agent, particularly a cytotoxic or otherwise anticellular agent, having the ability to kill or suppress the growth or cell division of cells.

As used herein, the terms "toxin" and "toxic moiety" are employed to refer to any cytotoxic or otherwise anticellular agent that has such a killing or suppressive property. Toxins are thus pharmacologic agents that can be conjugated to an antibody and delivered in an active form to a cell, wherein they will exert a significant deleterious effect.

The preparation of immunotoxins is, in general, well known in the art (see, e.g., U.S. Pat. No. 4,340,535, incorporated herein by reference). It also is known that while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Exemplary anticellular agents include chemotherapeutic agents, radioisotopes as well as cytotoxins. Example of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan.

Preferred immunotoxins often include a plant-, fungal- or bacterial-derived toxin, such as an A chain toxin, a ribosome inactivating protein, α-sarcin, aspergillin, restrictocin, a ribonuclease, diphtheria toxin or *pseudomonas* exotoxin, to mention just a few examples The use of toxin-antibody constructs is well known in the art of immunotoxins, as is their attachment to antibodies. Of course, combinations of the various toxins could also be coupled to one antibody molecule, thereby accommodating variable or even enhanced cytotoxicity.

One type of toxin for attachment to antibodies is ricin, with deglycosylated ricin A chain being particularly preferred. As used herein, the term "ricin" is intended to refer to ricin prepared from both natural sources and by recombinant means. Various 'recombinant' or 'genetically engineered' forms of the ricin molecule are known to those of skill in the art, all of which may be employed in accordance with the present invention.

Deglycosylated ricin A chain (dgA) is preferred because of its extreme potency, longer half-life, and because it is economically feasible to manufacture it a clinical grade and scale. Truncated ricin A chain, from which the 30 N-terminal amino acids have been removed by Nagarase (Sigma), also may be employed.

Linking or coupling one or more toxin moieties to an antibody may be achieved by a variety of mechanisms, for example, covalent binding, affinity binding, intercalation, coordinate binding and complexation. Preferred binding methods are those involving covalent binding, such as using chemical cross-linkers, natural peptides or disulfide bonds.

The covalent binding can be achieved either by direct condensation of existing side chains or by the incorporation of external bridging molecules. Many bivalent or polyvalent agents are useful in coupling protein molecules to other proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

In preferred embodiments, it is contemplated that one may wish to first derivatize the antibody, and then attach the toxin component to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α(2-pyridyldithio) toluene).

Biologically releasable bonds are particularly important to the realization of a clinically active immunotoxin in that the toxin moiety must be capable of being released from the antibody once it has entered the target-cell. Numerous types of linking constructs are known, including simply direct disulfide bond formation between sulfhydryl groups contained on amino acids such as cysteine, or otherwise introduced into respective protein structures, and disulfide linkages using available or designed linker moieties.

Numerous types of disulfide-bond containing linkers are known which can successfully be employed to conjugate toxin moieties to antibodies, however, certain linkers are generally preferred, such as, for example, sterically hindered disulfide bond linkers are preferred due to their greater stability in vivo, thus preventing release of the toxin moiety prior to binding at the site of action. A particularly preferred cross-linking reagent is SMPT, although other linkers such as SATA, SPDP and 2-iminothiolane also may be employed.

Once conjugated, it will be important to purify the conjugate so as to remove contaminants such as unconjugated A chain or antibody. It is important to remove unconjugated A chain because of the possibility of increased toxicity. Moreover, it is important to remove unconjugated antibody to avoid the possibility of competition for the antigen between conjugated and unconjugated species. In any event, a number of purification techniques have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation. To eliminate the free (unconjugated) toxin (e.g., dgA) a molecular exclusion chromatography step may be used using either conventional gel filtration procedure or high performance liquid chromatography.

After a sufficiently purified conjugate has been prepared, one will generally desire to prepare it into a pharmaceutical composition that may be administered parenterally. This is done by using for the last purification step a medium with a suitable pharmaceutical composition. Such formulations will typically include pharmaceutical buffers, along with excipients, stabilizing agents and such like. The pharmaceutically acceptable compositions will be sterile, non-immunogenic and non-pyrogenic. Details of their preparation are well known in the art and are further described herein. It will be appreciated that endotoxin contamination should be kept minimally at a safe level, for example, less that 0.5 ng/mg protein.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate.

As mentioned above, the cancer marker antibodies of the invention may be linked to one or more chemotherapeutic agents, such as anti-tumor drugs, cytokines, antimetabolites, alkylating agents, hormones, nucleic acids and the like, which may thus be targeted to a CD26 antigen expressing cancer cell using the antibody conjugate. The advantages of antibody-conjugated agents over their non-antibody conjugated counterparts is the added selectivity afforded by the antibody.

In analyzing the variety of chemotherapeutic and pharmacologic agents available for conjugating to an antibody, one may wish to particularly consider those that have been previously shown to be successfully conjugated to antibodies and to function pharmacologically. Exemplary antineoplastic agents that have been used include doxorubicin, daunomycin, methotrexate, vinblastine. Moreover, the attachment of other agents such as neocarzinostatin, macromycin, trenimon and α-amanitin has also been described. The lists of suitable agents presented herein are, of course, merely exemplary in that the technology for attaching pharmaceutical agents to antibodies for specific delivery to tissues is well established.

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent, as described above for the immunotoxins. Attachment also may be achieved by means of an acid labile acyl hydrazone or cis aconityl linkage between the drug and the antibody, or by using a peptide spacer such as L-Leu-L-Ala-L-Leu-L-Ala, between the γ-carboxyl group of the drug and an amino acid of the antibody.

E. Immunological Detection a. Immunoassays

The therapeutic anti-CD26 antibodies, are also useful in various diagnostic and prognostic applications connected with the detection and analysis of cancer. In still further embodiments, the present invention thus contemplates immunodetection methods for binding, purifying, identifying, removing, quantifying or otherwise generally detecting biological components. Thus, one may for example, combine or follow up the anti-CD26 antibody therapy of the invention with a round of immunodetection to obtain a prognosis or diagnosis of the efficacy of therapy reflected by the decrease in the number of CD26 expressing cancer cells.

The steps of various useful immunodetection methods have been described in the scientific literature, such as, e.g., Nakamura et al. (1987), incorporated herein by reference. Immunoassays, in their most simple and direct sense, are binding assays. Certain preferred immunoassays are the various types of enzyme linked immunosorbent assays (ELISAs), radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a sample suspected of containing a CD26 antigen or related cancer marker protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a cancer-specific antigen, e.g., CD26 antigen, such as a T-cell cancer, melanoma, glioblastoma, astrocytoma and carcinoma of the breast, gastric, colon, pancreas, renal, ovarian, lung, prostate, hepatic, lung, lymph node or bone marrow tissue section or specimen, a homogenized tissue extract, an isolated cell, a cell membrane preparation, separated or purified forms of any of the above protein-containing compositions, or even any biological fluid that comes into contact with cancer tissues, including blood, lymphatic fluid, seminal fluid and urine.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present, such as CD26 antigen. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. References concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of cancer. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

(i) ELISAs

As noted, it is contemplated that an immunodetection technique such as an ELISA may be useful in conjunction with detecting presence of CD26 on a clinical sample to determine the need for an anti-CD26 antibody treatment. Alternatively, one may use such a technique in embodiments where a cancer cell is induced to express CD26 to enable a treatment as provided herein.

In one exemplary ELISA, antibodies binding to the encoded proteins of the invention are immobilized onto a selected surface exhibiting protein affinity, such as a well in a polystyrene microtiter plate. Then, a test composition suspected of containing the cancer disease marker antigen, e.g., CD26 antigen, such as a clinical sample, is added to the wells. After binding and washing to remove non-specifically bound immunocomplexes, the bound antigen may be detected.

Detection is generally achieved by the addition of a second antibody specific for the target protein, that is linked to a detectable label. This type of ELISA is a simple "sandwich ELISA". Detection also may be achieved by the addition of a second antibody, followed by the addition of a third antibody that has binding affinity for the second antibody, with the third antibody being linked to a detectable label.

In another exemplary ELISA, the samples suspected of containing the CD26 antigen, are immobilized onto the well surface and then contacted with the antibodies of the invention. After binding and washing to remove non-specifically bound immunecomplexes, the bound antibody is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides, such as CD26 antigen, are immobilized, involves the use of antibody competition in the detection. In this ELISA, labeled antibodies are added to the wells, allowed to bind to the CD26 antigen, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

In other embodiments, solution-phase competition ELISA is also contemplated. Solution phase ELISA involves attachment of CD26 antigen to a bead, for example a magnetic bead. The bead is then incubated with sera from human and animal origin. After a suitable incubation period to allow for specific interactions to occur, the beads are washed. The specific type of antibody is the detected with an antibody indicator conjugate. The beads are washed and sorted. This complex is the read on an appropriate instrument (fluorescent, electroluminescent, spectrophotometer, depending on the conjugating moiety). The level of antibody binding can thus by quantitated and is directly related to the amount of signal present.

(ii) Immunohistochemistry

The anti-CD26 antibodies may be used in conjunction with both fresh-frozen and formalin-fixed, paraffin-embedded tissue blocks prepared from study by immunohistochemistry (IHC). For example, each tissue block consists of 50 mg of residual "pulverized" tumor. The method of preparing tissue blocks from these particulate specimens has been successfully used in previous IHC studies of various prognostic factors, e.g., in breast, and is well known to those of skill in the art (Brown et al., 1990; Abbondanzo et al., 1990; Allred et al., 1990).

Briefly, frozen-sections may be prepared by rehydrating 50 ng of frozen "pulverized" tumor at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

(iii) FACS Analyses

Fluorescent activated cell sorting, flow cytometry or flow microfluorometry provides the means of scanning individual cells for the presence of an antigen, such as CD26 antigen. The method employs instrumentation that is capable of activating, and detecting the excitation emissions of labeled cells in a liquid medium.

FACS is unique in its ability to provide a rapid, reliable, quantitative, and multiparameter analysis on either living or fixed cells. Cells would generally be obtained by biopsy, single cell suspension in blood or culture. FACS analyses would probably be most useful when desiring to analyze a number of cancer antigens at a given time, e.g., to follow an antigen profile during disease progression.

(iv) In Vivo Imaging

The invention also provides in vivo methods of imaging cancer using antibody conjugates. The term "in vivo imaging" refers to any non-invasive method that permits the detection of a labeled antibody, or fragment thereof, that specifically binds to cancer cells located in the body of an animal or human subject.

The imaging methods generally involve administering to an animal or subject an imaging-effective amount of a detectably-labeled cancer-specific antibody or fragment thereof (in a pharmaceutically effective carrier), such as a anti-CD26 antibody, and then detecting the binding of the labeled antibody to the cancerous tissue. The detectable label is preferably a spin-labeled molecule or a radioactive isotope that is detectable by non-invasive methods.

An "imaging effective amount" is an amount of a detectably-labeled antibody, or fragment thereof, that when administered is sufficient to enable later detection of binding of the antibody or fragment to cancer tissue. The effective amount of the antibody-marker conjugate is allowed sufficient time to come into contact with reactive antigens that be present within the tissues of the patient, and the patient is then exposed to a detection device to identify the detectable marker.

Antibody conjugates or constructs for imaging thus have the ability to provide an image of the tumor, for example, through magnetic resonance imaging, x-ray imaging, computerized emission tomography and the like. Elements particularly useful in Magnetic Resonance Imaging ("MRI") include the nuclear magnetic spin-resonance isotopes $^{157}$Gd, $^{55}$Mn, $^{162}$Dy, $^{52}$Cr, and $^{56}$Fe, with gadolinium often being preferred. Radioactive substances, such as technicium$^{99m}$ or indium$^{111}$, that may be detected using a gamma scintillation camera or detector, also may be used. Further examples of metallic ions suitable for use in this invention are $^{123}$I, $^{131}$I, $^{131}$I, $^{97}$Ru, $^{67}$Cu, $^{67}$Ga, $^{125}$I, $^{68}$Ga, $^{72}$As, $^{89}$Zr, and $^{201}$TI.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140-2000 keV range, which may be readily detected by conventional gamma cameras.

A radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA).

Administration of the labeled antibody may be local or systemic and accomplished intravenously, intra-arterially, via the spinal fluid or the like. Administration also may be intradermal or intracavitary, depending upon the body site under examination. After a sufficient time has lapsed for the labeled antibody or fragment to bind to the diseased tissue, in this case cancer tissue, for example 30 min to 48 h, the area of the subject under investigation is then examined by the imaging technique. MRI, SPECT, planar scintillation imaging and other emerging imaging techniques may all be used.

The distribution of the bound radioactive isotope and its increase or decrease with time is monitored and recorded. By comparing the results with data obtained from studies of clinically normal individuals, the presence and extent of the diseased tissue can be determined.

The exact imaging protocol will necessarily vary depending upon factors specific to the patient, and depending upon the body site under examination, method of administration, type of label used and the like. The determination of specific procedures is, however, routine to the skilled artisan. Although dosages for imaging embodiments are dependent upon the age and weight of patient, a one time dose of about 0.1 to about 20 mg, more preferably, about 1.0 to about 2.0 mg of antibody-conjugate per patient is contemplated to be useful.

F. COMBINATION CANCER THERAPIES

In order to further enhance the efficacy of the anti-CD26 antibody treatment provided by the invention, combination therapies are contemplated. Thus, a second therapeutic agent in addition to the anti-CD26 antibody based therapy may be used. The second therapeutic agent may be a chemotherapeutic agent, a radiotherapeutic agent, a gene therapeutic agent, a protein/peptide/polypeptide therapeutic agent, another immunotherapeutic agent, etc. Such agents are well known in the art.

Cancers that can be treated by the present invention include, but are not limited to, hematological malignancies including: B-cell chronic lymphocytic leukemia, or a B-cell lymphoma, lymphoblastic T-cell lymphoma, an acute lymphoblastic leukemia, a T-cell CD30+ anaplastic large cell lymphoma, a peripheral T-cell lymphoma, a T-cell chronic lymphocytic leukemia, an angioimmunoblastic T-cell lymphoma, an angiocentric T-cell lymphoma, an HTLV-related T-cell leukemia, or an adult T-cell leukemia, blood cancer, myeloid leukemia, monocytic leukemia, myelocytic leukemia, promyelocytic leukemia, myeloblastic leukemia, acute myelogenous leukemic, chronic myelogenous leukemic, lymphoblastic leukemia, hairy cell leukemia. Solid cell tumors and cancers that can be treated include those such as tumors of the brain (glioblastomas, medulloblastoma, astrocytoma, oligodendroglioma, ependymomas), lung, liver, spleen, kidney, lymph node, small intestine, pancreas, colon, stomach, breast, bone, endocrine glands, endometrium, prostate, testicle, thyroid, ovary, skin, head and neck, esophagus. Furthermore, the cancer may be a precancer, a metastatic and/or a non-metastatic cancer.

"Effective amount" is defined as an amount of the agent that will decrease, reduce, inhibit or otherwise abrogate the growth of a cancer cell, arrest-cell growth, induce apoptosis, inhibit metastasis, induce tumor necrosis, kill cells or induce cytotoxicity in cells.

The administration of the second therapeutic agent may precede or follow the therapy using anti-CD26 antibody by intervals ranging from minutes to days to weeks. In embodiments where the second therapeutic agent and the anti-CD26 antibody are administered together, one would generally ensure that a significant period of time did not expire between the time of each delivery. In such instances, it is contemplated that one would administer to a patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. It also is conceivable that more than one administration of either the second therapeutic agent and the anti-CD26 antibody will be required to achieve complete cancer cure. Various combinations may be employed, where the second therapeutic agent is "A" and the anti-CD26 antibody is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations also are contemplated. The exact dosages and regimens of each agent can be suitable altered by those of ordinary skill in the art.

Provided below is a description of some other agents effective in the treatment of cancer.

a) Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

b) Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

c) Chemotherapeutic Agents

Agents that damage DNA are chemotherapeutics. These can be, for example, agents that directly cross-link DNA, agents that intercalate into DNA, and agents that lead to chromosomal and mitotic aberrations by affecting nucleic acid synthesis. Agents that directly cross-link nucleic acids, specifically DNA, are envisaged and are exemplified by cisplatin, and other DNA alkylating agents. Agents that damage DNA also include compounds that interfere with DNA replication, mitosis, and chromosomal segregation.

Some examples of chemotherapeutic agents include antibiotic chemotherapeutics such as, Doxorubicin, Daunorubicin, Mitomycin (also known as mutamycin and/or mitomycin-C), Actinomycin D (Dactinomycin), Bleomycin, Plicomycin. Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. And other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Navelbine, Farnesyl-protein transferase inhibitors, Transplatinum, 5-Fluorouracil, and Methotrexate, Temazolomide (an aqueous form of DTIC), or any analog or derivative variant of the foregoing.

d) Other Immunotherapy

Other immunotherapeutics may be used in conjunction with the anti-CD26 antibody. Immunotherapeutics, generally, rely on the use of immune effector cells and molecules to target and destroy cancer cells. The other immune effector may be, for example, another antibody specific for some other marker on the surface of a tumor cell. This second antibody in itself may serve as an effector of therapy or it may recruit other cells to actually effecT-cell killing. This second antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T-cells and NK cells. Immunotherapy could be used as part of a combined therapy, in conjunction with the anti-CD26 antibody-based therapy.

The general approach for combined therapy is discussed below. In one aspect the immunotherapy can be used to target a tumor cell. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. Alternate immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with the anti-CD26 antibody-based therapy of this invention will enhance anti-tumor effects.

(i) Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

(ii) Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton et al., 1993).

(iii) Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro.

e) Gene Therapy

In yet another embodiment, gene therapy in conjunction with the anti-CD26 antibody therapy described in the invention are contemplated. A variety of nucleic acids and proteins encoded by nucleic acids are encompassed within the invention, some of which are described below. Table 1 lists various genes that may be targeted for gene therapy of some form in combination with the present invention.

TABLE 1

| Gene | Source | Human Disease | Function |
| --- | --- | --- | --- |
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases | | | |
| ERBB/HER | Avian erythroblastosis virus; ALV promoter insertion; amplified human tumors | Amplified, deleted squamous cell cancer; glioblastoma | EGF/TGF-α/ Amphiregulin/ Hetacellulin receptor |
| ERBB-2/NEU/HER-2 | Transfected from rat Glioblastomas | Amplified breast, ovarian, gastric cancers | Regulated by NDF/ Heregulin and EGF-Related factors |
| FMS | SM feline sarcoma virus | | CSF-1 receptor |
| KIT | HZ feline sarcoma virus | | MGF/Steel receptor Hematopoieis |

TABLE 1-continued

| Gene | Source | Human Disease | Function |
|---|---|---|---|
| TRK | Transfection from human colon cancer | | NGF (nerve growth Factor) receptor |
| MET | Transfection from human osteosarcoma | | Scatter factor/HGF Receptor |
| RET | Translocations and point mutations | Sporadic thyroid cancer; familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like transcription factor)/ PDGF receptor gene Fusion |
| TGF-β receptor | | Colon carcinoma mismatch mutation target | |
| NONRECEPTOR TYROSINE KINASES | | | |
| ABL | Abelson Mul. V | Chronic myelogenous leukemia translocation with BCR | Interact with RB, RNA polymerase, CRK, CBL |
| FPS/FES | Avian Fujinami SV; GA FeSV | | |
| LCK | Mul. V (murine leukemia virus) promoter insertion | | Src family; T-cell signaling; interacts CD4/CD8 T-cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |
| MISCELLANEOUS CELL SURFACE[1] | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and *Drosophilia* homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALL | Signaling? |
| MISCELLANEOUS SIGNALING | | | |
| BCL-2 | Translocation | B-cell lymphoma | Apoptosis |
| CBL | Mu Cas NS-1 V | | Tyrosine- Phosphorylated RING finger interact Abl |
| CRK | CT1010 ASV | | Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |
| GUANINE NUCLEOTIDE EXCHANGERS AND BINDING PROTEINS | | | |
| BCR | | Translocated with ABL in CML | Exchanger; protein Kinase |

TABLE 1-continued

| Gene | Source | Human Disease | Function |
|---|---|---|---|
| DBL | Transfection | | Exchanger |
| GSP | | | |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis Virus | | NF-κB family transcription factor |
| SKI | Avian SKV770 Retrovirus | | Transcription factor |
| VHL | Heritable suppressor | Von Hippel-Landau syndrome | Negative regulator or elongin; transcriptional elongation complex |
| WT-1 | | Wilm's tumor | Transcription factor |
| CELL CYCLE/DNA DAMAGE RESPONSE[10-21] | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (predisposition leukemia | |
| MDA-7 | Fragile site 3p14.2 | Lung carcinoma | Histidine triad-related diadenosine 5',3''''-tetraphosphate asymmetric hydrolase |
| hMLI/MutL | | HNPCC | Mismatch repair; MutL Homologue |
| hMSH2/MutS | | HNPCC | Mismatch repair; MutS Homologue |

TABLE 1-continued

| Gene | Source | Human Disease | Function |
|---|---|---|---|
| hPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; osteosarcoma; breast cancer; other sporadic cancers | Interact cyclin/cdk; regulate E2F transcription factor |
| XPA | | xeroderma pigmentosum; skin cancer predisposition | Excision repair; photo-product recognition; zinc finger | f) Other Agents

It is contemplated that other agents may be used in combination with the present invention to improve the therapeutic efficacy of treatment. One form of therapy for use in conjunction with chemotherapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen and this often reduces the risk of metastases.

G. Pharmaceuticals

Pharmaceutical compositions comprising effective amounts of anti-CD26 antibodies, or antibody conjugates, may be dissolved or dispersed in a pharmaceutically acceptable carrier or medium to form therapeutic and/or diagnostic formulations that may then be administered according to methods of the invention.

The therapeutic antibodies of the present invention can be formulated in standard pharmaceutical carriers for administration to patients in need thereof. These include saline, phosphate buffered saline, and other aqueous carriers, and liposomes, polymeric microspheres and other controlled release delivery devices, as are well known in the art.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds will generally be formulated for parenteral administration, e.g., formulated for injection via the intravenous, intraarthricular, intrathecal, intramuscular, sub-cutaneous, intra-lesional, or even intraperitoneal routes. The preparation of an aqueous composition that contains a cancer marker antibody, conjugate, inhibitor or other agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile indictable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose.

Dispersions can also be prepared in glycerol, liquid polyethylene glycols, and mixtures thereof and in oils. Under ordinary conditions of storage and use, these preparations contain a preservative to prevent the growth of microorganisms.

Formulations of neutral or salt forms are also provided. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the indictable compositions can be brought about by the use in the compositions of agents delaying absorption, for example, aluminum monostearate and gelatin.

Sterile indictable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile indictable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for local injection also is contemplated. In this regard, the use of DMSO as solvent is preferred as this will result in extremely rapid penetration, delivering high concentrations of the active agents to a small area.

Upon formulation, solutions will be administered in a manner compatible with the dosage formulation and in such amount as is diagnostically or therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In other embodiments, direct intratumoral injection is contemplated. Alternatively, the tumor may be infused or perfused with the therapeutic compounds using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is also contemplated.

In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated or diagnosed. The person responsible for administration will, in any event, determine the appropriate dose for the individual subject.

H. Routes of Administration

The routes of administration will vary, naturally, with the location and nature of the lesion, and include, e.g., intradermal, intrathecal, intraarthricular, transdermal, parenteral, intravenous, intra-arterial, intramuscular, intranasal, subcutaneous, percutaneous, intratracheal, intraperitoneal, intratumoral, perfusion, lavage, direct injection, topical application, and oral administration and formulation. Intratumoral injection, or injection into the tumor vasculature is specifically contemplated for discrete, solid, accessible tumors. Local, regional or systemic administration also may be appropriate. In the case of surgical intervention, the present invention may be used before surgery, at the time of surgery, and/or thereafter, to treat residual or metastatic disease. For example, a resected tumor bed may be injected or perfused with a formulation comprising the anti-CD26 antibody. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery may be via syringe or catherization. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumors will require more aggressive treatment, while at the same time, certain patients cannot tolerate more taxing protocols. The clinician will be best suited to make such decisions based on the known efficacy and toxicity (if any) of the therapeutic formulations.

In some embodiments, liposomal formulations comprising anti-CD26 antibodies are contemplated. Liposomal encapsulation of pharmaceutical agents prolongs their half-lives when compared to conventional drug delivery systems. Because larger quantities can be protectively packaged, this allow the opportunity for dose-intensity of agents so delivered to cells.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes. Liposomes are characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991) Also contemplated are cationic lipid-nucleic acid complexes, such as lipofectamine-nucleic acid complexes.

I. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In Vitro and In Vivo Antitumor Effects of an Anti-CD26 Monoclonal Antibody

Materials And Methods

Animals. Female C.B-17 SCID mice were obtained from Taconic Farms, Inc. at 3-4 weeks of age and were housed in microisolator cages, and all food, water and bedding were autoclaved before use.

Cells. The human CD30+ anaplastic large cell T-cell lymphoma cell line Karpas 299 was established from the peripheral blood blasT-cells of a 25-year-old white man with the diagnosis of CD30+ anaplastic large cell T-cell lymphoma, bearing surface markers CD4, CD5, HLA-DR and CD30, with the t(2;5) translocation and with rearranged T-cell receptor beta-chain gene (Fischer et al., 1988; Tian et al., 1995). Cells were incubated at 37° C. in culture medium, consisting of RPMI 1640 supplemented with 10% FCS, penicillin (100 units/ml) and streptomycin (100 µg/ml) (GIBCO BRL, Rockville, Md.).

Antibodies. The Anti-CD26 monoclonal antibodies (mAbs) used are 1F7 and 5F8, both of which are murine antibodies recognizing human CD26 and have been described previously (Morimoto et al., 1989; Dang et al., 1990b; Torimoto et al., 1992). Control mAb used is an isotype control mouse IgG1 recognizing a CD45 RA epitope not expressed on Karpas 299 cell line and was developed as described previously (Morimoto et al., 1989). Anti-CD3 and anti-CD2 mAbs were purchased from Coulter. For Western blotting studies, anti-p21 and anti-p27 were obtained from Transduction Laboratories; anti-p53 was obtained from Calbiochem; anti-cdk2, anti-cdk4, anti-cyclin D were obtained from Upstate Biotechnology; anti-cyclin E and anti-PCNA were obtained from Santa Cruz Biotechnology; and anti-actin was obtained from Sigma.

Reagents. Tetrazolium salt MTT (3,(4,5-dimethylthiazol-2-yl)2,5-diphenyltetrazolium bromide) (Sigma) was dissolved at a concentration of 5 mg/ml in sterile PBS at room temperature, with the solution being further sterilized by filtration and stored at 4° C. in the dark. Extraction buffer was prepared as follows: 20% w/v of SDS was dissolved at 37° C. in a solution of 50% each of N,N-dimethyl formamide (DMF) (Sigma) and distilled water; pH was adjusted to 4.7 by the addition of 1M HCl. Cycloheximide CHX (Sigma) was used at a concentration of 20 µg/ml.

In Vivo Studies

All mice were pretreated intraperitoneally with 0.2 ml of anti-asilo GM1 polyclonal antisera 25% (v/v) (Wako, Richmond, Va.) 1 day before tumor transplant to eliminate host natural killer cell activity and facilitate tumor engraftment (Tian et al., 1995). For survival studies, tumor cells were then inoculated by i.p. injection. 1 day following tumor cell inoculation, SCID mice then received saline, isotype control Ab or anti-CD26 mAb 1F7 i.p. injections in 0.1 ml sterile saline at the indicated doses and schedules. Tumor-bearing mice were then monitored for tumor development and progression, and moribund mice were euthanized and necropsied for evidence of tumors. In addition, mice with visible or palpable tumors measuring 2 cm at its greatest dimension were also euthanized and necropsied to minimize suffering to the animals. For some animals, organs were also harvested for histopathologic analyses. In some studies, SCID mice were injected with tumor cells by s.c. injection and after tumor size has reached 0.5 cm at its greatest dimension, saline or 1F7 (5 µg per injection) was injected intratumorally every other day for 7 injections. Mice were then euthanized, and tumor mass at the site of injection was harvested for histopathologic analyses.

In other studies, SCID mice were injected with $1 \times 10^6$ Karpas 299 tumor cells incubated in saline alone, 100 µg of 1F7 or isotype control Ab by s.c. injection. Subsequently, starting 1 day after tumor cell inoculations, SCID mice were given saline, isotype control Ab (20 µg/injection) or 1F7 (20 µg/injection) s.c. injections in 0.1 ml sterile saline every other day for 10 injections, placed at the original site of s.c. tumor injection. The day of initial appearance of a visible tumor was documented to evaluate treatment effects.

In Vitro Studies

MTT Assay. Cell growth assay was performed as described previously (Hansen et al., 1989). Cells were incubated in microplates in the presence of culture medium alone or culture medium plus antibodies as described, to a total volume of 100 µl (50,000 cells/well). Following 48 hours of incubation at 37° C., 25 µl of MTT was added to the wells at a final concentration of 1 mg/ml. The microplates were then incubated for 2 hours at 37° C., followed by the addition of 100 µl of extraction buffer. Following overnight incubation at 37° C., OD measurements at 570 nm were performed. Values reported represent the means of triplicate wells, and the standard errors of the mean were less than 15%.

Immunofluorescence. All procedures were carried out at 4° C., and flow cytometry analyses were performed (FACScan, Becton Dickinson) as previously described (Dang et al., 1990d). Cells were stained with the appropriate antibodies, washed 2 times with PBS, and then with goat anti-mouse IgG FITC. Cells were then washed 2 times with PBS prior to flow cytometry analyses. Negative controls were stained with second antibody alone. For some studies, SCID mice were inoculated with tumor cells i.p. ($1 \times 10^6$ cells/mouse) as described above. When tumors were palpable, animals were euthanized and tumor mass was harvested. Single cell suspensions were then isolated from tumor mass, and flow cytometry was then performed.

Cell Cycle Analysis. Cells were incubated in either medium alone or in the presence of antibodies at a concentration of 5 µg/ml at 37° C. At the appropriate time intervals, cells were collected, washed twice with PBS and resuspended in PBS containing 10 µg/ml propidium iodide, 0.5% Tween-20 and 0.1% RNase at room temperature for 30 minutes. Samples were then analyzed (FACScan, Becton Dickinson) for DNA content. Cell debris and fixation artifacts were gated out and G0/G1, S and G2/M populations were quantified using the CellQuest and ModFit LT programs.

SDS-PAGE and Immunoblotting. After incubation at 37° C., cells were harvested from wells, washed with PBS and lysed in lysis buffer, consisting of 1% Brij 97, 5 mM EDTA, 0.02 M HEPES pH 7.3, 0.15 M NaCl, 1 mM PMSF, 0.5 mM NaF, 10 µg/ml aprotinin, and 0.2 mM sodium orthovanadate. After incubating on ice for 15 minutes, nuclei were removed by centrifugation and supernatants were collected. 2× Sample buffer consisting of 20% glycerol, 4.6% SDS, 0.125 M Tris, pH 6.8 and 0.1% Bromophenol Blue was added to the appropriate aliquots of supernatants. Protein samples were submitted to SDS-PAGE analysis on a 20% gel under standard conditions using a mini-Protean II system (Bio-Rad Hercules, Calif.). For immunoblotting, the proteins were transferred onto nitrocellulose (Immobilon-P, Millipore). Following overnight blocking at 4° C. in blocking solution consisting of 0.1% Tween 20 and 5% bovine serum albumin in TBS, membranes were blotted with the appropriate primary antibodies diluted in blocking solution for 1 hour at room temperature. Membranes were then washed with blocking solution, and appropriate secondary antibodies diluted in blocking solution were then applied for 1 hour at room temperature. Secondary antibodies were goat anti-mouse or goat anti-rabbit HRP conjugate (Dako). Membranes were then washed with blocking solution and proteins were subsequently detected by chemiluminescence (Amersham Pharmacia Biotech).

Results

Figure 1B:
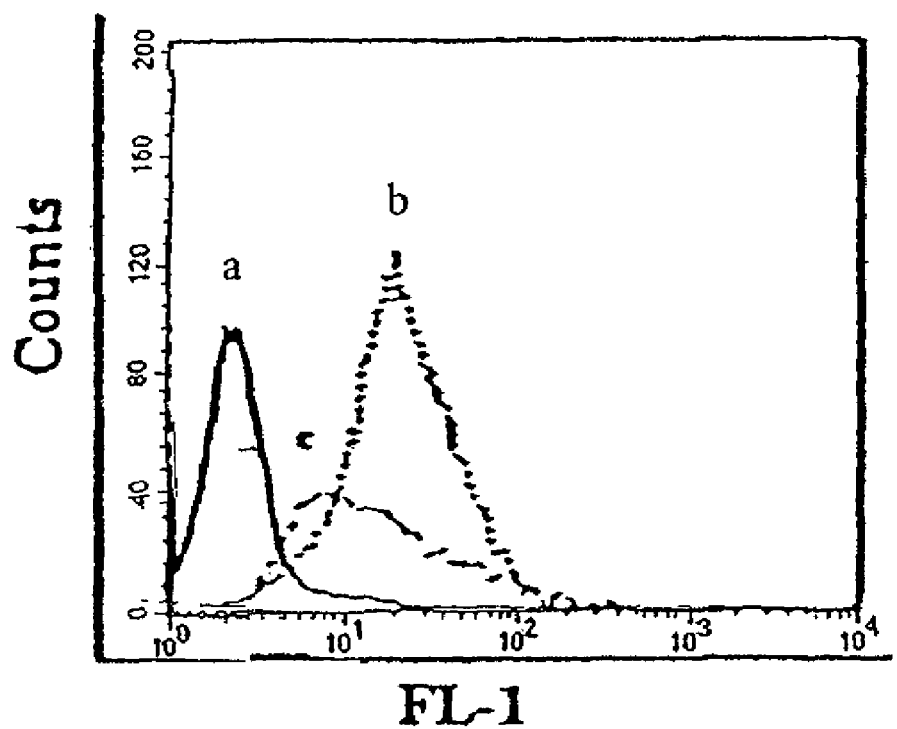
(FIG. 1B) Following overnight incubation with the anti-CD26 mAb 1F7 (1 µg/ml) at 37° C., Karpas 299 cells were evaluated for CD26 expression and compared to CD26 expression before overnight incubation with 1F7. a=negative control, b=before anti-CD26 treatment, c=after anti-CD26 treatment.

CD26 Expression on the Karpas 299 Lymphoma Cell Line. Expression of CD26 on the CD30+ anaplastic large cell T-cell lymphoma cell line Karpas 299 was evaluated by flow cytometry prior to tumor implantation into the SCID mouse. As shown in FIG. 1A, Karpas 299 cells have high surface expression of CD26, while CD3 and CD2 surface expression is not detectable. In addition, overnight incubation with 1F7 led to a decrease in expression of CD26 surface expression (FIG. 1B), consistent with previously reported findings of anti-CD26-mediated modulation of CD26 surface expression on normal T-cells (Dang et al., 1990d).

Figure 2A:
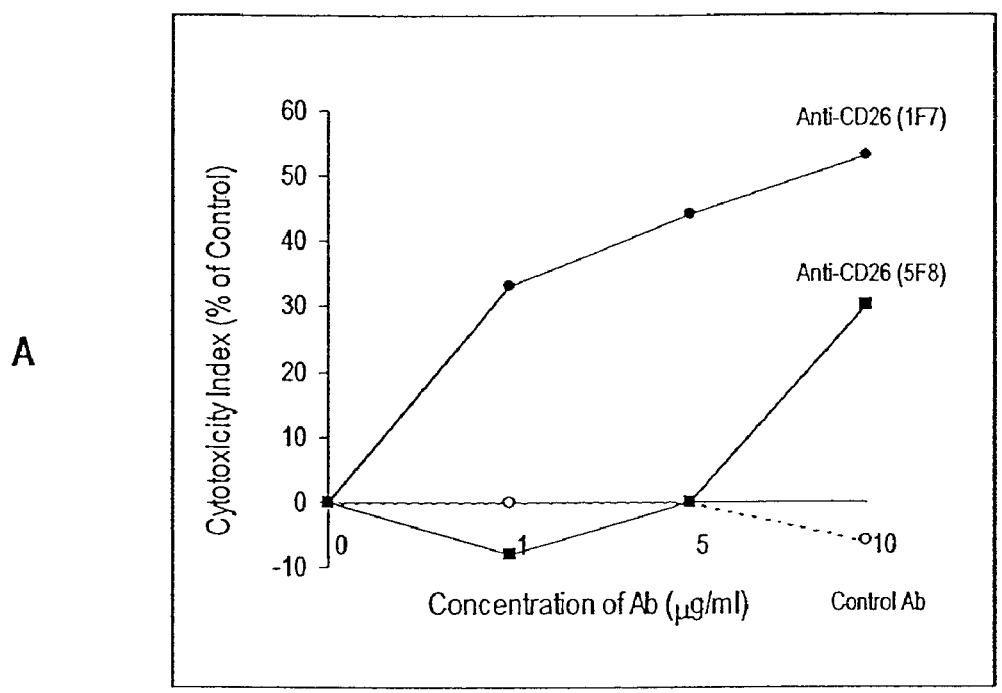
FIGS. 2A. & 2B. Inhibitory effect of soluble anti-CD26 mAb on cell growth. Karpas 299 cells (FIG. 2A) and H9 cells (FIG. 2B) were incubated with media containing soluble anti-CD26 mAb 1F7, anti-CD26 mAb 5F8 or isotype control mAb, and MTT uptake assay was performed. Data are representative of three experiments for each cell line. Cytotoxicity index (% of Control)=1−OD of treated cells×100−OD of cells incubated in cell culture medium alone.
Figure 2B:
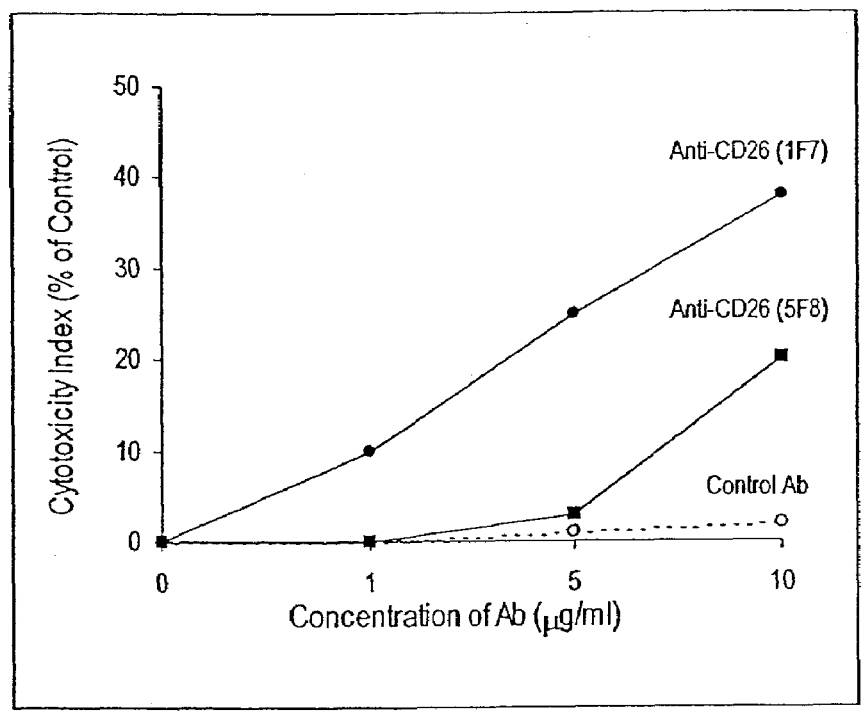

CD26-Mediated Inhibition of Cell Growth at the G1/S Checkpoint. The effect of soluble anti-CD26 antibody binding on growth of Karpas 299 cells and H9 cells were examined in in vitro studies. As shown in FIG. 2A. and FIG. 2B., the addition of 1F7 resulted in decreased cell growth as measured by MTT reduction. The 5F8 monoclonal antibody also exerted significant inhibitory effect on cell growth, however, higher concentrations of 5F8 were used in comparison to 1F7. The anti-CD26 mAbs did not exert any growth inhibitory effect on CD26-negative cell lines at the concentrations tested. Additional evidence of the inhibitory effect of 1F7 on cell growth was obtained through cell cycle analysis. As shown in Table 2, binding of 1F7 resulted in enhanced blockade of cell cycle progression at the G1/S checkpoint, leading eventually to decreased cell metabolism and cell growth as detected by reduction in MTT uptake.

TABLE 2

Anti-CD26-mediated cell cycle arrest at G1/S

| | % G0/G1 | | | % S | | | % G2/M | | |
|---|---|---|---|---|---|---|---|---|---|
| | Media | Control Ab | 1F7 | Media | Control Ab | 1F7 | Media | Control Ab | 1F7 |
| Day 1 | 26.71 | 25.04 | 36.04 | 47.81 | 47.52 | 35.98 | 25.48 | 27.44 | 27.98 |
| Day 2 | 56.55 | 53.81 | 73.52 | 24.71 | 25.96 | 14.04 | 18.74 | 20.23 | 12.44 |

Karpas 299 cells were incubated at 37° C. with media or antibodies (2 µg/ml). At the indicated time intervals, cells were harvested and cell cycle analyses were performed. Data are representative of three separate studies.

Enhancement of p21 Expression Following CD26-Mediated Cell Cycle Arrest. In view of the integral role played by cyclin-dependent kinase inhibitors at the G1/S checkpoint, the expression of p21, p27 and p16 following anti-CD26 antibody binding was examined. Enhanced p21 expression following anti-CD26 treatment was shown in Karpas 299 cells were incubated overnight at 37° C. with either media alone, media containing isotype control mAb or 1F7 (2 µg/ml), cells were then harvested, and SDS-PAGE and immunoblotting studies were performed. In other experiments, Karpas 299 cells were treated with 1F7 (2 µg/ml) or media alone at various time intervals and p21 expression was detected. It was found that p27 expression is not affected by anti-CD26 mAb binding, and that p16 expression was not detectable in cells incubated in medium alone or in the presence of control antibodies as well as anti-CD26 mAbs. On the other hand, p21 expression was enhanced following CD26 ligation. Compared to incubation under control conditions, treatment with anti-1F7 resulted in increased expression of p21. Western blotting with an anti-p21 mAb showed the appearance of the expected band migrating at the 21 kd position. It is known that under certain conditions, induction of p21 expression is dependent on p53 (El-Deiry et al., 1993; El-Deiry et al., 1994). In the Karpas 299 cell line, no change in p53 expression was seen in anti-CD26-treated cells when compared with controls. However, the functional status of p53 has not yet been determined.

It is known that p21 forms complexes with cyclins and CDKs to inhibit cell cycle progression at G1/S. Although, anti-CD26 antibody binding enhanced p21 expression, protein levels of cyclin D, cyclin E, cdk2 and cdk4, all of which are present within the cyclin/CDK/p21 complex, remain unchanged. In addition, PCNA protein levels were unaffected by treatment with anti-CD26. Similar data were obtained following anti-CD26 binding to the CD26+ H9 cell line. It was also shown that enhanced p21 expression is detected within 3 hours of treatment with 1F7, with its level rising during continued antibody treatment.

Enhanced p21 Expression is Dependent on de novo Protein Synthesis. To determine whether the enhancement in p21 expression following anti-CD26 binding is dependent on increased protein synthesis, p21 expression was examined in the presence and absence of the protein synthesis inhibitor cycloheximide (CHX). p21 expression was seen in the cells treated with 1F7 but not in those treated with 1F7 and CHX. Thus, expression of p21 following CD26 ligation is dependent on de novo protein synthesis.

Figure 3A:
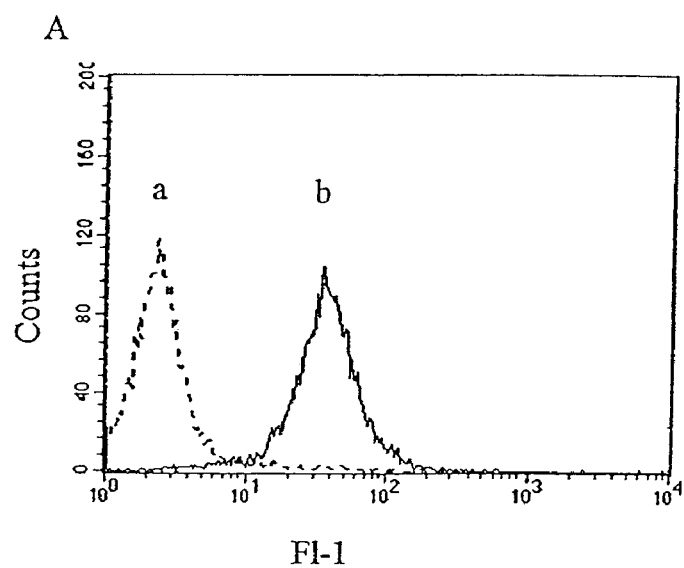
FIGS. 3A. & 3B. CD26 surface expression on Karpas 299 cells following tumor formation in SCID mouse.
Figure 3B:
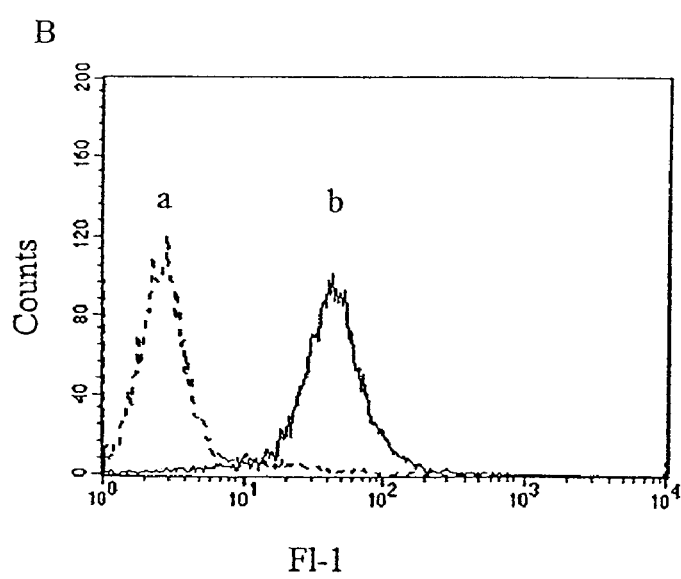

Anti-Tumor Effects of 1F7 in SCID Mice Bearing Karpas 299 in an in vivo Tumor Model. The effect of the anti-CD26 mAb 1F7 on Karpas 299 growth was also examined in a SCID mouse tumor model. For this, $1 \times 10^6$ Karpas 299 cells were implanted by i.p. injection into the SCID mouse, and tumors were allowed to develop. Subsequently, the tumor mass was removed and single cell suspensions were established. The process of tumor formation in the in vivo model did not effect CD26 surface expression. For example, as shown in FIG. 3A & FIG. 3B, CD26 expression following tumor implantation into the SCID mouse was similar to its level prior to tumor implantation. Postmortem histopathologic analyses of tissue sections of the intraperitoneal mass also showed the presence of CD26.

Figure 4A:
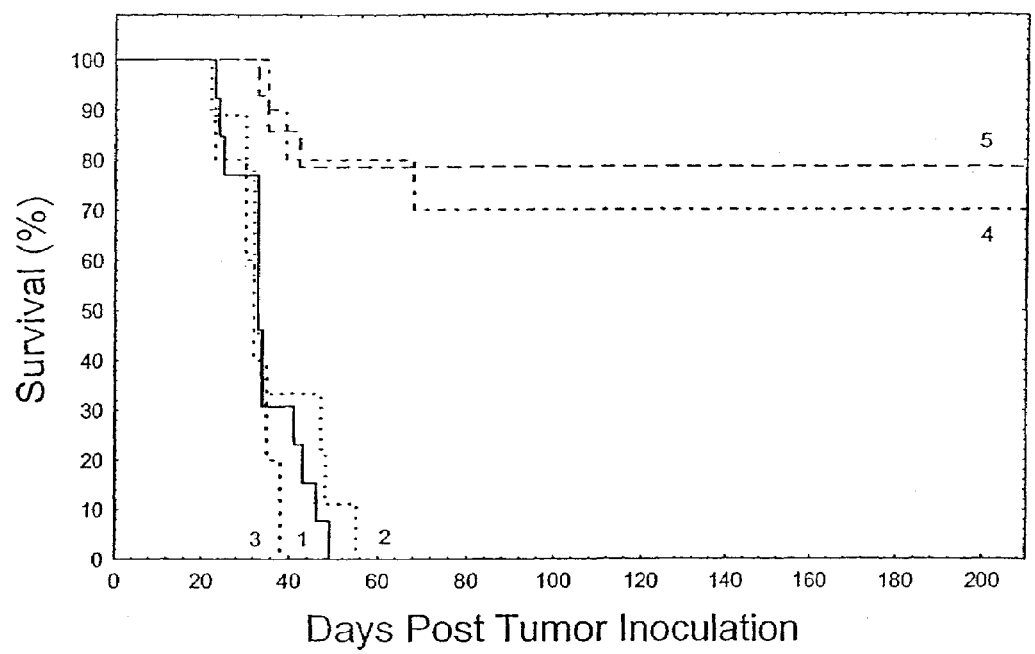
FIGS. 4A. & 4B. Enhanced survival of Karpas 299-bearing SCID mice following 1F7 treatment.

SCID mice were then inoculated with Karpas 299 cells by i.p. injection ($1 \times 10^6$ cells/mouse) and starting at day 1 after tumor inoculation, treatment with saline, isotype control Ab or 1F7 was started at the indicated doses every other day for a total of 10 i.p. injections. As shown in FIG. 4A, mice treated with 1F7 at 5 µg/injection had statistically significant survival advantage over those treated with saline ($p<0.0001$) or isotype control Ab at 5 µg/injection ($p<0.001$). Similarly, the survival advantage of mice treated with 1F7 at 10 µg/injection was statistically significant as compared to saline-treated mice ($p<0.0001$) or mice treated with isotype control Ab at 10 µg/injection ($p<0.001$). The data also shows no statistically significant difference in survival between 1F7 doses of 5 µg/injection and 10 µg/injection ($p=0.7$).

Mice that were injected with higher i.p. doses of tumor cells ($3 \times 10^6$ cells/mouse) and then subsequently treated by i.p injections of saline alone, isotype control Ab (20 µg/injection) or 1F7 at doses of 5 µg/injection ($p<0.05$), 10 µg/injection ($p<0.05$) or 20 µg/injection ($p<0.01$) given every other day for a total of 10 injections, again showed no statistically significant survival advantage over mice treated initially injected with lower doses of tumor cells. Mice treated at 1F7 dose of 20 µg/injection had statistically significant survival advantage over those treated with isotype control Ab at a dose of 20 µg/injection ($p<0.01$).

Figure 4B:
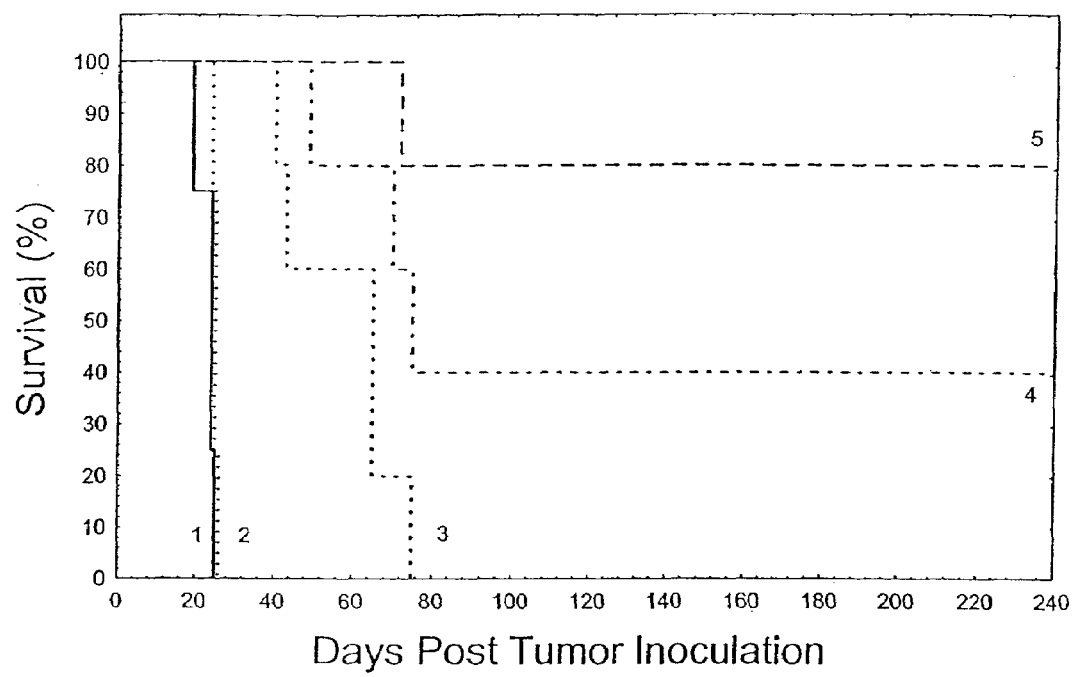

Comparing mice treated with different 1F7 doses, those treated with 20 µg/injection had statistically significant survival advantage over those treated with 1F7 dose of 5 µg/injection ($p<0.01$). There was also a trend for greater survival advantage for mice treated with 1F7 at a dose of 20 µg/injection when compared to those treated at a dose of 10 µg/injection ($p=0.2$). Likewise, there was a trend for greater survival advantage for those treated with 1F7 dose of 10 µg/injection as compared to 5 µg/injection ($p=0.09$) (FIG. 4B). These data indicate that the efficacy of antibody treatment was dependent on the relative amount of tumor present.

Postmortem histopathologic analyses of tissue sections showed that tumor bearing mice treated under control conditions developed tumor infiltrates at local sites as well as distant organs. On the other hand, 1F7-treated mice had no evidence of tumor involvement at these sites. Thus, the anti-CD26 antibody also prevents metastatic tumor growth.

The antitumor effect of 1F7 in the SCID mouse model were also demonstrated. For this, SCID mice were inoculated with $1 \times 10^6$ Karpas 299 cells by s.c. administration. Following the development of a visible tumor mass, mice were then treated by intratumoral injections of either saline alone or 1F7 (5 µg/injection) given every other day for 7 injections. Histopathologic analyses showed that 1F7 treatment resulted in tumor necrosis, as most of the tumor had undergone coagulative necrosis. In contrast, saline treatment resulted in tumor cells being viable in the vast majority of the tumor mass. Treatment with isotype control Ab at 5 µg/injection led to similar results as those obtained with saline treatment, as most of the tumor cells were found to be viable in the tumor mass.

The time required for initial appearance of Karpas 299 tumors following s.c. injection of tumor cells and s.c. treatment with saline, 1F7 or isotype control Ab was also determined. For these studies, SCID mice were injected s.c. with $1 \times 10^6$ Karpas 299 cells incubated in saline alone, 100 µg of 1F7 or 100 µg of isotype control Ab. Subsequently, starting 1 day after tumor cell inoculations, SCID mice then received saline, isotype control Ab (20 µg/injection) or 1F7 (20 µg/injection) s.c. injections in 0.1 ml sterile saline every other day for 10 injections, placed at the original site of s.c. tumor injection. The day of initial appearance of a visible tumor was documented to evaluate treatment effects.

Figure 5:
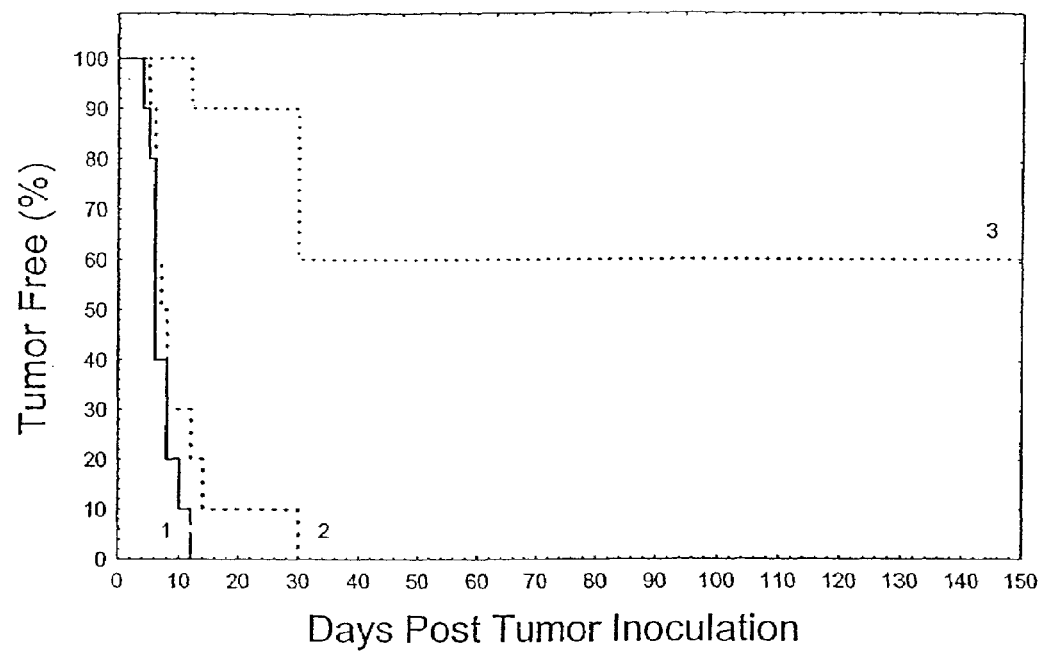
FIG. 5. Initial tumor appearance in SCID mice following s.c. tumor cell inoculation and s.c. treatment with antibodies. SCID mice were injected with 1×10$^6$ Karpas 299 tumor cells incubated in saline alone, 100 μg of 1F7 or isotype control Ab by s.c. injection. Subsequently, starting 1 day after tumor cell inoculations, SCID mice then received saline, isotype control Ab (20 μg/injection) or 1F7 (20 μg/injection) s.c. injections in 0.1 ml sterile saline every other day for 10 injections, placed at the original site of s.c. tumor injection. The day of initial appearance of a visible tumor was documented to evaluate treatment effects. Arm 1: saline alone (n=10); arm 2: isotype control Ab (n=10); arm 3: anti-CD26 mAb 1F7 (n=10).

As shown in FIG. 5, there was a statistically significant difference in the rate of visible tumor development among the mice treated with different conditions. The group treated with 1F7 had a lower rate of tumor development than those treated with isotype control Ab or saline alone ($p<0.001$ and $p<0.001$, respectively), with the majority of 1F7-treated mice remaining free of tumor during the length of the study.

Example 2

Anti-CD26 MAb 1F7 Inhibits T Lymphocyte Proliferation and Arrests Cell Cycle at G1/S Associated with Enhanced $p21^{Cip1}$ Expression Methods Preparation and Culture of Cells. Human T-cell clones were established by in vitro stimulation of human peripheral blood lymphocytes according to the methods described previously (Sugita et al., 1992). Human Jurkat T-cell line was obtained from ATCC. The Jurkat cell lines include: 1) wild type CD26-transfected Jurkat cell lines (J. C26/DP+), 2) Jurkat cell lines transfected with mutant CD26 containing an alanine at the putative catalytic serine residue at position 630, resulting in a mutant CD26-positive/DPPIV-negative Jurkat transfectant (J.C26/DP−), and 3) non-transfected parental Jurkat cells (Jwt) (Tanaka et al., 1992; Tanaka et al., 1993). Jurkat transfectants were incubated at 37° C. at a concentration of $1 \times 10^6$/ml in culture media, consisting of RPMI 1640 (Life Technologies Inc., Grand Island, N.Y.) supplemented with 10% FCS, penicillin (100 units/ml), streptomycin (100 µg/ml) (Life Technologies Inc.), and G418 (500 µg/ml) (Sigma-Aldrich, St. Louis, Mo.). Non-transfected parental Jurkat cells were maintained in the same culture media without G418. Human peripheral blood mononuclear cells (PBMC), collected from healthy adult volunteers, were isolated by centrifugation on Ficoll/Paque (Amersham Pharmacia Biotech., Piscataway, N.J.). To obtain a highly purified T-cell population, PBMC were separated into an E rosette-positive population and were used as resting T-cells as determined by flow cytometric analysis (FAScalibur™, Nippon Becton Dickinson Co., Ltd., Tokyo, Japan) using an FITC-labeled anti-CD3 mAb (BD PharMingen, San Diego, Calif.), with purity being >95%. T-cell clones were maintained in culture media containing IL-2 (10 ng/ml; PepRoTech EC Ltd., London, U.K.), and restimulated every 2-3 weeks with irradiated (30Gy) allogeneic PBMC ($1.0 \times 10^5$/ml) (Sugita et al., 1992). Viability of cells was examined using trypan blue (Sigma-Aldrich) dye exclusion method.

Antibodies and Reagents. Anti-CD26 mAbs, 1F7 and 5F8, and isotype control mAb 4B4 (CD29 mAb) are previously described (Morimoto et al., 1989; Torimoto et al., 1992; Morimoto et al., 1985, incorporated herein by reference). Anti-CD3 mAb (OKT3) is also described elsewhere (Kung et al., 1979, incorporated herein by reference). The following antibodies and reagents were purchased from BD PharMingen: FITC labeled anti-bromodeoxyuridine (BrdU), anti-$p21^{Cip1}$, anti-$p27^{Kip1}$, anti-p53, anti-cyclin D1, anti-CDK4, anti-CDK-6, anti-ERK, and 7-aminoactinomycin D (7-AAD). Mouse monoclonal anti-phosphotyrosine 4G10, and anti-β-actin were purchased from Sigma-Aldrich, and anti-phosphorylated ERK was from Santa Cruz (Delaware Avenue, Calif.). The source and working concentration of reagents used for cell stimulation and inhibition of signal transduction are as follows: OKT3 (0.05 µg/ml), PMA (10 ng/ml; Sigma-Aldrich), Nocodazole (500 ng/ml from 1 mg/ml stock solution in DMSO; Sigma-Aldrich), PD98059 (10 µM from 10mM stock solution in DMSO; BIOMOL, Plymouth Meeting, Pa.), and U0126 (10 µM from 1 mM stock solution in DMSO; Cell Signaling Technology Inc., Beverly, Mass.). Cells were treated with each inhibitors 30 minutes before initiation of culture with mAbs.

Flow Cytometry Analysis. All procedures were carried out at 4° C., and flow cytometry (FCM) analyses were performed with FACSCalibur™ (Nippon Becton-Dickinson) using standard CELLQuest™ acquisition/analysis software (Becton-Dickinson). Cells were stained with the appropriate antibodies, and washed two times with ice-cold PBS prior to FCM analysis.

Cell Cycle Analysis. Cells ($1 \times 10^6$/well) were incubated in media alone or in the presence of 1F7, 5F8 or isotype control mAb (4B4) at indicated concentrations with or without Nocodazole at 37° C. In experiments using inhibitors, $1 \times 10^6$ cells were incubated with various inhibitors at the indicated concentrations for 30 minutes at 37° C. prior to incubation with anti-CD26 mAbs. At the appropriate time interval, cells were pulsed with BrdU at a concentration of 10 µM for final 1 hour at 37° C. Cells were then collected and washed twice with ice-cold PBS. Fixation, permeabilization, and immunostaining of cells by FITC labeled anti-BrdU and 7-AAD were performed according to the BD PharMingen instruction manual of BrdU Flow Cytometry Kit. Samples were then analyzed by FACSCalibur™ within 1 hour after preparation. By the region gates applied to BrdU versus 7-AAD dot plot after gating out cell debris and fixation artifacts, FCM analysis allowed for the discrimination of cell subsets that resided in G0/G1, G2/M, and S phases of the cell cycle. G0/G1, S and G2/M populations were quantified using the CELLQueSt™ program (Becton-Dickinson).

Preparation of Cell Lysates and Western Blot Analysis. After incubation at 37° C., cells were harvested from wells, washed with PBS and lysed in RIPA lysis buffer, consisting of 1% NP-40, 0.5% sodium deoxycholate, 0.1% SDS, 5 mM EDTA, 10 mM Tris-HCl (pH 7.4), 0.15 M NaCl, 1 mM PMSF, 0.5 mM NaF, 10 µg/ml aprotinin and 0.02 mM $Na_3VO_4$. For detecting phosphotyrosine proteins, cells after incubation were washed with ice-cold PBS containing 5 mM EDTA, 10 mM, NaF, 10 mM Na-pyrophosphate and 0.4 mM $Na_3VO_4$. Cells were centrifuged and then solubilized in lysis buffer (1% NP-40, 0.5% sodium deoxycholate, 5 mM EDTA, 50 mM Tris-HCl (pH 8.0), 0.15M NaCl, 1 mM PMSF, 10 mM iodacetamide, 10 mM NaF, 10 µg/ml aprotinin and 0.4 mM $Na_3VO_4$). After removal of precipitation by ultracentrifugation, cell lysates were then submitted to SDS-PAGE analysis on an appropriate concentration gel under reducing condition using a mini-Protean II system (Bio-Rad Laboratories, Hercules, Calif.). For immunoblotting, the proteins were transferred to a polyvinylidene difluoride membrane (Immobilon-P; Millipore, Bedford, Mass.) in 25 mM Tris, 192 mM glycine, and 20% methanol, and the membrane was blocked for 1 hour at room temperature in PBS with 0.05% Tween 20 containing 5% non-fat milk. Specific antigens were probed by the corresponding mAbs, followed by HRP-conjugated anti-mouse Ig (Amersham Pharmacia). Western blots were visualized by the enhanced chemiluminescence technique (NEN, Boston, Mass.).

In Vitro Cell Proliferation Assay. Cell proliferation was determined using $[^3H]$-thymidine incorporation (ICN Radiochemicals, Irvine, Calif.). All proliferation assays of each experiment were performed in triplicate. $0.2 \times 10^6$ of cells in each microplate well were incubated in the presence of media alone or in the presence of 1F7 (1 µg/ml) at 37° C. with or without stimulation of OKT3 and PMA. After being incubated for 72 hours, cells were pulsed with $[^3H]$-thymidine (1 µCi/well) for the final 8 hours of culture. Cells were then harvested onto a glass filter (Wallac, Turk, Finland), and radioactivity was counted using a liquid scintillation counter (Wallac). $[^3H]$-thymidine uptake was expressed as the mean cpm of triplicate samples.

Statistics. Student's t test was used to determine whether the difference between control and sample was significant ($p<0.05$ being significant).

Results

Figures 6A, 6B, 6C:
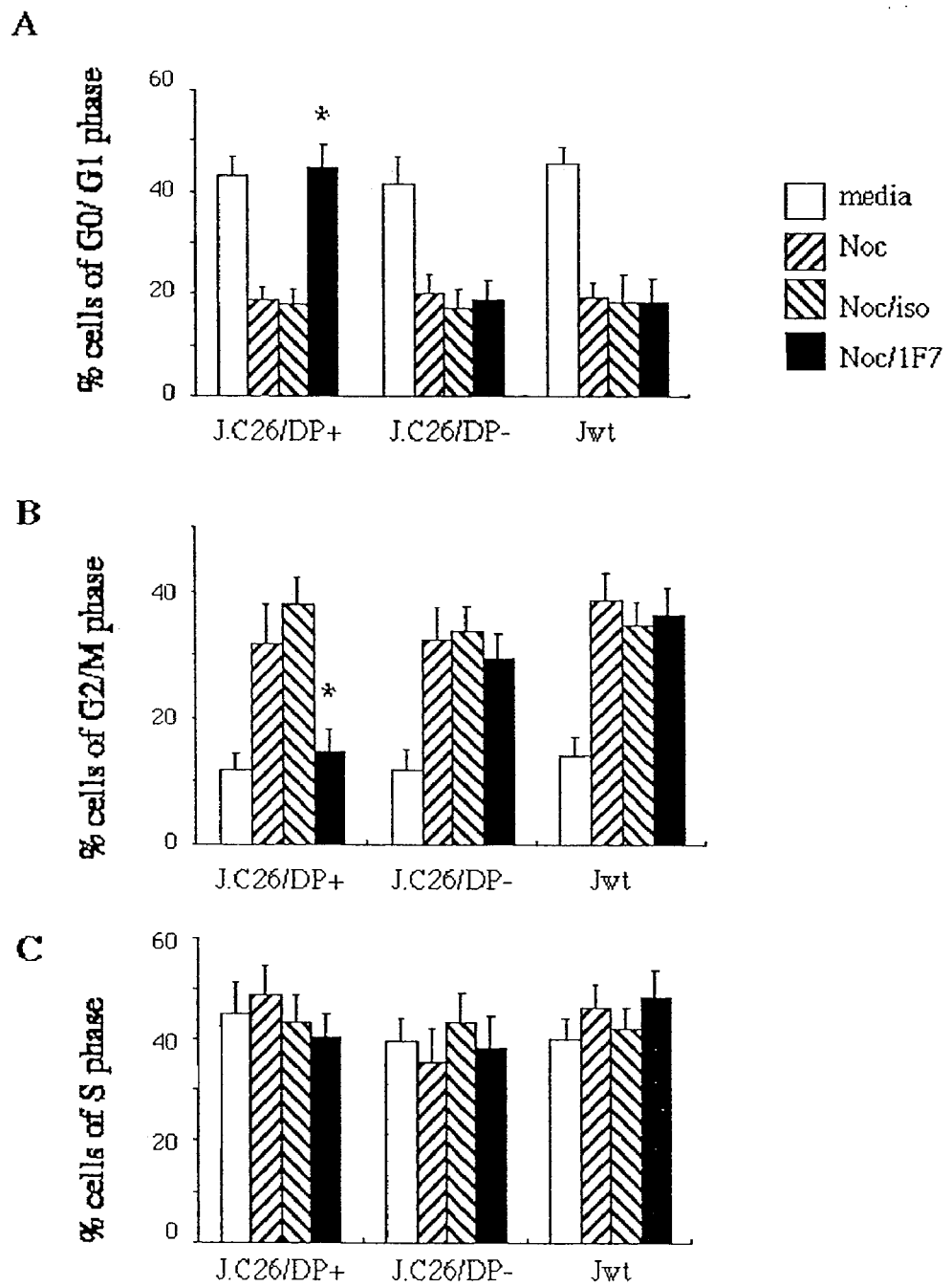
FIGS. 6A, 6B & 6C. Treatment of CD26 transfected Jurkat T-cells with anti-CD26 mAb 1F7 resulted in cell cycle arrest at G1/S. J.C26/DP+ were incubated with media alone, isotype control mAb 4B4 (Iso) or 1F7 in the presence or absence of Nocodazole (Noc). Cell culture, staining and cell cycle analyses were performed as described in Materials and Methods. The measurement of G0/G1 (FIG. 6A), G2/M (FIG. 6B) and S (FIG. 6C) cells is shown. Bars are representative of mean values of percentage of G0/G1, G2/M and S cells±standard errors of three independently performed experiments. Asterisks indicate samples with results significantly different from those for J.C26/DP− and Jwt (p<0.05).

Anti-CD26 MAb Treatment Inhibits Cell Cycle Progression at the G1/S Checkpoint. Effects of soluble anti-CD26 antibody binding on cell cycle of Jurkat cells transfected with cDNA of a CD26 with DPPIV active domain (J.C26/DP+), and without DPPIV active domain (J.C26/DP−) were examined (Tanaka et al., 1992; Tanaka et al., 1993). To analyze cell cycle status, FCM with two-color staining of FITC labeled-BrdU and 7-AAD after cells were pulsed with BrdU was used. To better visualize cell cycle effects, cells were treated with Nocodazole, which arrests cells in M phase unless they are arrested in G0/G1 phase. Cell viability validated by trypan blue dye exclusion method remained to be >95% in the presence or absence of Nocodazole. As shown in FIG. 6A, the addition of anti-CD26 mAb 1F7 to J.C26/DP+ resulted in blockade of cell cycle progression at the G1/S checkpoint. Of note is the fact that cell cycle arrest at the G1/S checkpoint was not observed in J.C26/DP− or parental Jurkat (Jwt) (FIG. 6A). In FIG. 6B, G2/M accumulation by Nocodazole was observed in 1F7 non-treated J.C26/DP+, but not in 1F7 treated J.C26/DP+. This effect of G2/M accumulation by Nocodazole was also observed in J.C26/DP− and Jwt in the presence or absence of 1F7 (FIG. 6B). On the other hand, S phase was not influenced by 1F7 treatment (FIG. 6C). These findings indicate that the effect of cell cycle progression at the G1/S checkpoint is dependent on the enzymatic activity of DPPIV intrinsic to the CD26 molecule.

Figure 7:
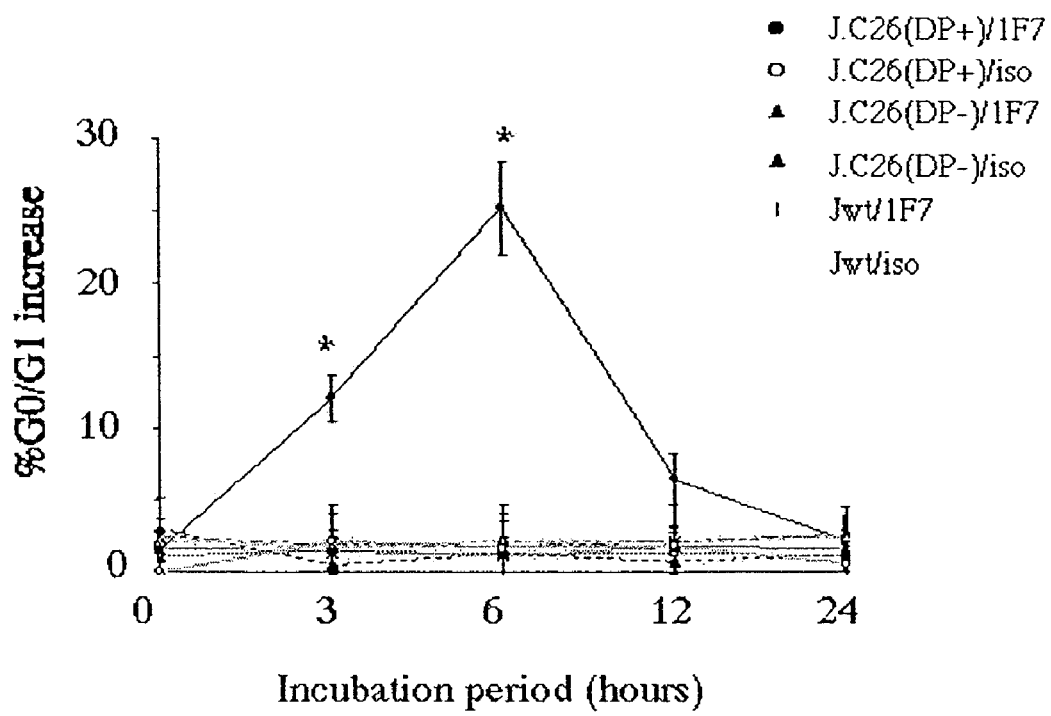
FIG. 7. Enhanced p21 expression following anti-CD26 mAb 1F7 treatment. Time course analysis of % G0/G1 increase following incubation with 1F7 in the presence of Nocodazole. Cell cycle analyses were performed as described in Materials and Methods. The percentage increase in G0/G1 is the difference in percent G0/G1 content between mAb and non-mAb treated cells. Bars are representative of mean values of % G0/G1 increase±standard errors of three independently performed experiments. Asterisks indicate samples with results significantly different from those for J.C26/DP− and Jwt (p<0.05).

Enhancement of p21 Expression Associated with Cell Cycle Arrest at the G1/S Checkpoint Following Anti-CD26 MAb Treatment. Close examination of the cellular response of Jurkat cells to 1F7 by FCM analysis revealed that J.C26/DP+ exhibited an approximately 25% increase in G1 arrest 6 hours after initiation of culture with 1F7 (FIG. 7). At 12 and 24 hours after 1F7 treatment, J.C26/DP+ gradually lost their initial G0/G1 arrest. Notably, in J.C26/DP−, cell cycle arrest was not observed. These findings again indicate that the effect on cell cycle progression at the G1/S checkpoint is dependent on the enzymatic activity of DPPIV. The effect of 1F7 was dose-dependent at concentrations 0.1-10.0 μg/ml. It should be noted that another anti-CD26 mAb 5F8 recognizing a distinct CD26 epitope from 1F7 had no such effect as observed with 1F7 (Torimoto et al., 1992).

Because cell cycle arrest can be accompanied by increases in CDKI and/or decreases in cyclins or CDKs, the expression of various cell cycle regulatory proteins following 1F7 binding was examined. Compared to incubation under control conditions (media alone or 4B4 as isotype matched control mAb treatment), treatment of J. C26/DP+ with 1F7 resulted in increased expression of $p21^{Cip1}$ shown by Western blotting analysis of the relative levels of the protein.

For the Western blotting, J.C26/DP+ and J.C26/DP− were incubated with 1F7. Cells were then harvested at the indicated periods of culture, and expression of $p21^{Cip1}$ was assessed by Western blotting with the appropriate mAbs. Equal loading of cell extracts was confirmed using anti-β-actin mAb. No effect on $p21^{Cip1}$ expression was observed with media alone or 4B4. Treatment of J.C26/DP− with 1F7 did not result in increased expression of $p21^{Cip1}$. Enhanced $P_{21}^{Cip1}$ expression was detected within 6 hours of treatment with 1F7, and then gradually decreased, being compatible with the cell cycle analysis shown in FIG. 6A.

Further, J.C26/DP+ and J.C26/DP− were incubated with media alone, isotype control mAb 4B4 (Iso) or 1F7 for 6 hours. Cells were then harvested, and expression of $p21^{Cip1}$, $p27^{Kip1}$, p53, cyclin D1, CDK4, and CDK6 was assessed by Western blotting with the appropriate mAbs. Equal loading of cell extracts was confirmed using anti-β-actin mAb. In contrast to $p21^{Cip1}$, the expression of Cyclin D1, CDK4, CDK6, $p27^{Kip1}$, and p53, which are associated with G1-regulation cyclin complex, did not change at 6 hours after treatment with 1F7.

It should be noted that the expression of these proteins did not change between 0-24 hours after initiation of culture with 1F7. These results indicate that 1F7 stimulation leads to upregulation of $p21^{Cip1}$ and cell cycle arrest at the G1/S checkpoint through the DPPIV enzymatic activity of CD26.

MEK-ERK Pathway Plays an Important Role in 1F7-Mediated Cell Cycle Arrest at the G1/S Checkpoint. CD26 molecules were also shown to be present in membrane lipid rafts and ligation of CD26 by 1F7 was shown to increase the recruitment of CD26 molecules to rafts (Ishii et al., 2001). T-cell receptors (TCR) in lipid rafts also interacts with other signaling molecules (Janes et al., 1999; Cheukuri et al., 2001), thereby inducing increased tyrosine phosphorylation of signaling molecules. CD26 is involved in essential T-cell signaling events through its physical and functional association with key cellular structures (Morimoto and Schlossman, 1998; von Bonin et al., 1998; De Meester et al., 1999). Other studies demonstrated that hyperactivation of the Raf-MEK-ERK pathway in T-cells and other cell lineages led to alterations in the expression of key cell cycle regulators and cell cycle arrest at the G1/S check point (Boussiotis et al., 1997; Sewing et al., 1997; Chen et al., 1999). Therefore, tyrosine phosphorylation of signaling molecules related to CD26 in T-cells was examined with respect to expression of $p21^{Cip1}$. J.C26/DP+, J.C26/DP− and Jwt were incubated with 1F7 for the various time periods, i.e., 0, 5, and 10 minutes. Cells were then harvested, separated by 5-20% gradient SDS-PAGE, and the status of tyrosine phosphorylation was assessed by Western blotting with the anti-phosphotyrosine mAb 4G10 (pY). Equal loading of cell extracts was confirmed using an Ab that recognizes β-actin. 1F7 treatment of J.C26/DP+ induced tyrosine phosphorylation of proteins with molecular weights of approximately 40 kDa at 5 to 10 minutes after initiation of culture. However, no induction in tyrosine phosphorylation was observed following 1F7 treatment in J.C26/DP− and Jwt. These changes were not observed in experiments using isotype matched control mAb 4B4.

To characterize the 40 kDa phosphorylated protein, the phosphorylation status of ERK was examined, since previous work showed that the Raf-MEK-ERK pathway mediates anti-CD3 mAb-induced G1 arrest (Chen et al., 1999). ERK proteins were shown to be phosphorylated following treatment of J.C26/DP+ with 1F7. For this experiment, J.C26/DP+ were incubated with media alone, isotype control mAb 4B4 (Iso) or 1F7 for the various time periods, i.e., 0, 5 and 10 minutes. Cell lysates were blotted with anti-phospho-ERK, and reprobed with anti-ERK mAb. No difference was observed with experiments using J.C26− or Jwt.

To confirm these results, the effect of inhibiting the MEK-ERK pathway on $p21^{Cip1}$ expression was examined. Cells were treated with 1F7 for 6 hours in the absence or presence of the MEK-specific inhibitor PD98059. The enhanced expression of $p21^{CiP1}$ associated with phosphorylation of ERK was clearly inhibited by the presence of the MEK inhibitor. It should be noted that equal loading of the gel lanes was confirmed by probing the Western blots with an antibody that recognizes ERK. These results suggested that induction of $p21^{Cip1}$ following 1F7 treatment was mediated via the MEK-ERK pathway.

Figure 8:
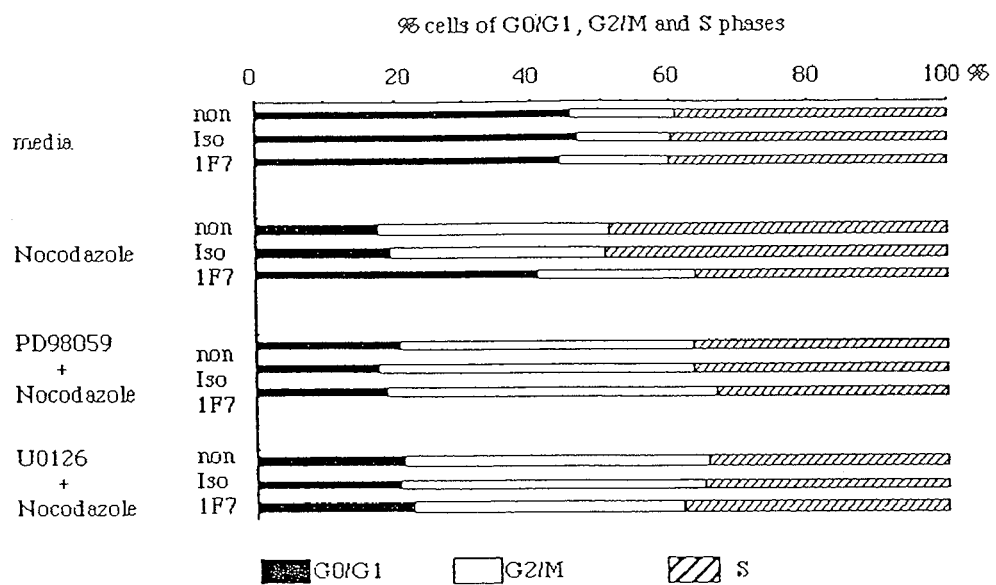
FIG. 8. Phosphorylation of ERK resulted in enhanced p21$^{Cip1}$ expression following anti-CD26 mAb 1F7 treatment. J.C26/DP+ cells were incubated with media alone, isotype control mAb 4B4 (Iso) or 1F7 in the presence or absence of Nocodazole after incubation with MEK kinase inhibitors PD98059 and U0126. After a 6-hour incubation, cell cycle analyses were performed as described in in Materials and Methods. Data are representative of three independently performed experiments. No effect of PD98059 and U0126 on G0/G1 arrest was observed in J.C26- or Jwt.

To further determine the role of the MEK-ERK pathway in cell cycle regulation of T-cells after treatment with 1F7, cell cycle analysis by FCM was performed in the absence or presence of the MEK-specific inhibitors PD98059 and U0126. Consistent with results regarding $p21^{Cip1}$ expression, G0/G1 arrest of 1F7-treated J.C26/DP+ was disrupted by the presence of the MEK specific inhibitors (FIG. 8), which was not observed in J.C26/DP− and Jwt. These findings indicate that anti-CD26 treatment induced cell cycle arrest at G1/S checkpoint in T-cells by activating MEK-ERK pathway, leading to enhanced expression of the CDKI $p21^{Cip1}$.

Figure 9:
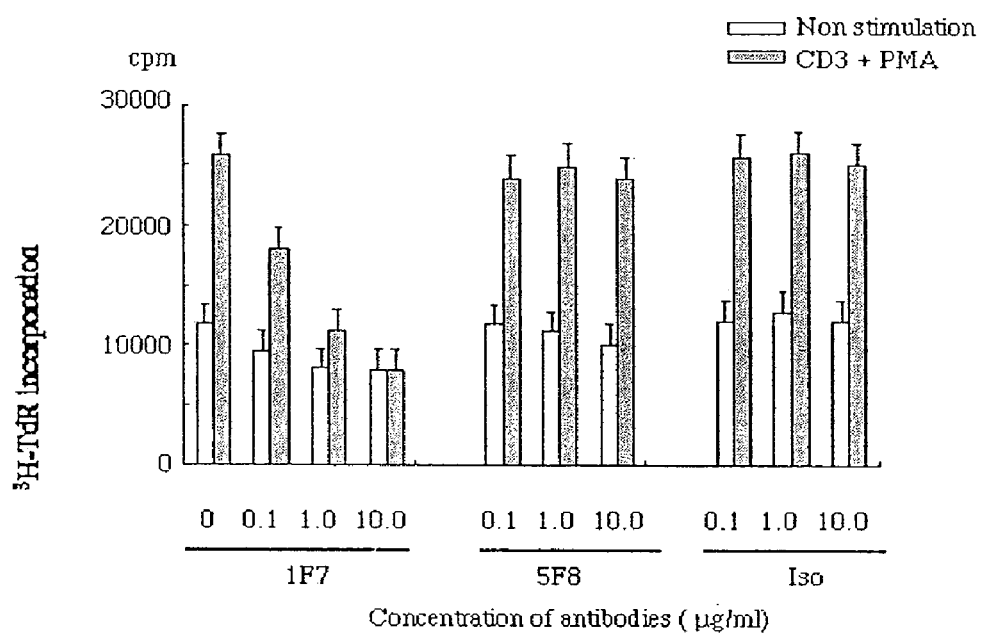
FIG. 9. Inhibition of cell proliferation by the anti-CD26 mAb 1F7 on human T-cell clones with enhancement of p21$^{Cip1}$ expression. Human T clones were incubated with media or media containing the anti-CD26 mAbs 1F7 or 5F8, or isotype control mAb 4B4 (Iso) at the indicated concentrations, with or without stimulation by anti-CD3 mAb (OKT3) and PMA. 0.2*10$^5$ cells were incubated and were pulsed with [$^3$H]-thymidine. [$^3$H]-thymidine incorporation was expressed as the mean cpm of triplicate samples with standard errors.

Anti-CD26 MAb 1F7 Treatment Inhibits Proliferation of T-cell Clones. Upregulation of $p21^{Cip1}$ has been described during T-cell proliferation and in CD4+ memory T-cells of autoimmune-prone BXSB (Nourse et al., 1994; Sabzevari et al., 1997). Moreover, $p21^{Cip1}$-deficient mice accumulated abnormal amounts of CD4+ memory T-cells and developed loss of tolerance towards nuclear antigens (Sabzevari et al., 1997). In view of these findings, to define the biological effect of 1F7-mediated $p21^{Cip}$ enhancement on the proliferation of human peripheral T-cells, the effect of soluble anti-CD26 antibody binding on proliferation of human T-cell clones derived from PBMC was examined. As shown in FIG. 9, the addition of 1F7 to human T-cell clones resulted in a reduction of cellular proliferation, as assayed by [$^3$H]-thymidine uptake. Of note is the fact that there was no inhibitory effect following treatment with the anti-CD26 mAb 5F8 (Morimoto et al., 1992; Dong et al., 1998), or an isotype control antibody 4B4. Similar to results described above in experiments using Jurkat transfectants, $p21^{Cip1}$ expression in T-cell clones was also enhanced following treatment with 1F7 (FIG. 4B). 1F7 effect of enhanced $p21^{Cip1}$ expression was also observed in PHA blast T-cells, albeit to a lesser degree, but not in resting T-cells. For this experiment, T-cell clones, 10-day PHA blast T-cells, and freshly isolated T-cells were incubated for 72 hours with media alone or 1F7. Cell lysates were then prepared for Western blotting with mAbs recognizing $p21^{Cip1}$. Equal loading of cell extracts was confirmed using mAbs that recognize β-actin. These results indicate that in activated T-cells such as T-cell clones and PHA blast T-cells, T-cell proliferation was inhibited by the treatment of 1F7 via the induction of $p21^{Cip1}$.

The inventors have demonstrated that anti-CD26 mAb 1F7 binding led to cell cycle arrest at the G1/S check point, and that engagement of CD26 induced G1 arrest on CD26 Jurkat transfectants through enhanced expression of the cell cycle regulatory protein $p21^{Cip1}$. This effect is mediated by activation of the MEK-ERK pathway. In addition to CD26 Jurkat transfectants, inhibition of proliferation and enhancement of $p21^{Cip1}$ expression was also observed in T-cell clones and PHA blast T-cells derived from human PBMC.

The antigen sensitivity of class II MHC-restricted human CD4+ T-cell clones is demonstrated to increase gradually with time after stimulation. This is manifest by requirement of less antigen in culture, as well as decreased numbers of peptide-MHC complexes per antigen-presenting cells (APC) for T-cell activation, and increased resistance to inhibition by class II MHC blockade (Lehaman et al., 1989). It was previously demonstrated that the increase in antigen sensitivity was accompanied by increased cell-surface expression of CD26, LFA-1 and VLA-1, whereas the expression of TCR and a series of other T-cell surface molecules remains unchanged (Falcioni et al., 1996). The present invention also demonstrates that the late-memory T-cell phenotype occurs among T-cells activated in vivo. Moreover, using appropriate mAbs, treatment by CD26 mAb with MHC blockade is demonstrated to contribute to inhibition of proliferation of activated memory T-cells (Falcioni et al., 1996). Furthermore, the molecular mechanism of the inhibitory effect of T-cell proliferation by anti-CD26 mAb has been shown to be via cell cycle arrest at G1/S check point and induction of $p21^{Cip1}$ by activation of MEK-ERK pathway.

In addition, CD26 molecules in T-cells exist in membrane lipid rafts, hence, cross-linking of CD26 with anti-CD26 mAbs induces aggregation of CD26 molecules into lipid rafts. This process results eventually in the activation of T-cells through tyrosine phosphorylation of signaling molecules, such as Cb1, ZAP-70, ERK, $p56^{Lck}$ and CD3-zeta (Ishii et al., 2001). TCR also exerts its signaling effects through the recruitment of various surface and cytosolic adapter proteins into lipid rafts (Janes et al., 1999; Cheukuri et al., 2001). As negative regulators of TCR signaling, Rap1, Raf and Cb1-b have been shown to aggregate in lipid rafts (Boussiotis et al., 1997; Sewing et al., 1997, Leo and Schraven, 2001). Relating to this point, it has been demonstrated that increased intensity of Raf-MEK-ERK signaling can eliciT-cell cycle arrest at G1/S check point associated with an increase in the expression of $p21^{Cip1}$. Meanwhile, high dose of anti-CD3 mAb induced cell cycle arrest by activating the Raf-MEK-ERK pathway, leading to the expression of $p21^{Cip1}$ in T-cells and a failure to down-regulate the expression of $p27^{kip1}$ (Sewing et al., 1997; Chen et al., 1999).

Accumulating evidence suggests that DPPIV enzyme activity plays an essential role in CD26-mediated T-cell costimulation as well as T-cell immune responses (Morimoto and Schlossman, 1998; von Bonin et al., 1998; De Meester et al., 1999).

The present invention shows that DPPIV enzyme activity plays a role in the induction of $p21^{Cip1}$ following treatment of T-cells with the anti-CD26 mAb 1F7. It is reported that CD26/DPPIV regulates various cellular functions by cleaving selected chemokines at the N-terminus to modify their biological functions (De Meester et al., 1999; Oravecz et al., 1997; Proost et al., 1998). In view of its ability to cleave certain biological factors as a serine protease, it is conceivable that DPPIV enzyme activity of CD26 appears to regulate phosphorylation of ERK and induction of $p21^{Cip1}$ through cleavage of relevant biological factors in T-cells. Experiments aimed at identifying the CD26/DPPIV-associated factors responsible for regulating the expression of $p21^{Cip1}$ are contemplated.

The finding that 1F7 has a more potent effect than 5F8 demonstrated that engagement of selected epitopes of CD26 is an important factor in mediating cell cycle arrest, inhibiting cell proliferation and inducing $p21^{Cip1}$ expression following mAb treatment. It should also be noted that 1F7 has a strong co-mitogenic capacity whereas 5F8 has no such activity (Dong et al., 1998). Thus, the epitopes recognized by 1F7 and 5F8 on the CD26 molecule have distinct functional effects.

Activated memory T-cells express high levels of CD26, and this phenotype of late-memory T-cells is associated with both in vivo and in vitro increased antigen sensitivity (Falcioni et al., 1996). In vivo studies revealed that a large number of CD26+ T-cells are found in inflamed tissues of patients with multiple sclerosis and rheumatoid arthritis (Mizokami et al., 1996; Eguchi et al., 1989; Hafler et al., 1985), indicating that CD26+ T-cells function as effector T-cells. Thus, CD26 is useful as an immunotherapy agent. In fact, anti-CD26 treatment was reported to be effective in decreasing the incidence of steroid-resistant acute GVHD after allogeneic bone marrow transplantation (Bacigalupo et al., 1985; De Meester et al., 1993), although the precise mechanism involved in these clinical results is not yet elucidated. The present data indicate that cell cycle regulation of activated T-cells via CD26 is useful for controlling both T-cell cancers and leukemias as well as acute GVHD by inhibiting cellular proliferation. Taken together with the observation that transfection of p21 gene enhanced cyclosporin A-mediated inhibition of lymphocyte proliferation (Ashwani et al., 2000), anti-CD26 mAb therapy provides an alternative strategy to induce immunosuppression, one that is potentially less toxic than the side effects currently seen with conventional agents. Thus, anti-CD26 antibodies are effective as anti-cancer agents as well as immunosuppressive agents.

Example 3

Clinical Trials

This section is concerned with the development of human treatment protocols for anticancer therapy using the anti-CD26 antibodies either alone or in combination with other therapeutic agents. Although only cancer related treatments are described here, this Example, is also applicable to the treatment of immune diseases such as autoimmunity, GVHD, and prevention of organ transplant rejection reactions.

The various elements of conducting a clinical trial, including patient treatment and monitoring, will be known to those of skill in the art in light of the present disclosure.

The following information is being presented as a general guideline for use in establishing the anti-CD26 antibody based therapies described herein alone or in combinations with other adjunct treatments used routinely in cancer therapy in clinical trials.

Candidates for the phase 1 clinical trial will be patients on which all conventional therapies have failed. Approximately 100 patients will be treated initially. Their age will range from 16 to 90 (median 65) years. Patients will be treated, and samples obtained, without bias to sex, race, or ethnic group. For this patient population of approximately 41% will be women, 6% will be black, 13% Hispanic, and 3% other minorities. These estimates are based on consecutive cases seen at MD Anderson Cancer Center over the last 5 years.

Optimally the patient will exhibit adequate bone marrow function (defined as peripheral absolute granulocyte count of >1,000/mm³ and platelet count of 100,000/mm³ (unless decreased due to tumor involvement in the marrow), adequate liver function (bilirubin ≦1.5 mg/dl, SGOT/SGPT <4× Upper Limit of Normal) and adequate renal function (creatinine ≦1.5 mg/dl).

Research samples will be obtained from peripheral blood or marrow under existing approved projects and protocols. Some of the research material will be obtained from specimens taken as part of patient care.

The anti-CD26 antibody treatments described above will be administered to the patients regionally or systemically on a tentative weekly basis. A typical treatment course may comprise about six doses delivered over a 7 to 21 day period. Upon election by the clinician the regimen may be continued with six doses every three weeks or on a less frequent (monthly, bimonthly, quarterly, etc.,) basis. Of course, these are only exemplary times for treatment, and the skilled practitioner will readily recognize that many other time-courses are possible.

The modes of administration may be local administration, including, by intratumoral injection and/or by injection into tumor vasculature, intratracheal, intrathecal, endoscopic, subcutaneous, and/or percutaneous. The mode of administration may be systemic, including, intravenous, intra-arterial, intra-peritoneal and/or oral administration.

The anti-CD26 antibody will be administered at dosages in the range of 1 µg/kg to 1 g/kg intravenously, although exact dosage will depend on subsequent testings. In some embodiments the antibodies are administered as liposomal formulations or potentially via other artificial carriers. Antibodies may also be administered as inactive moieties to be activated upon encountering CD26 expressing tumor cells. For example, a liposomal formulation of the antibody is administered a range of 0.01 to 100 mg/m²/day intravenously. Of course, the skilled artisan will understand that while these dosage ranges, provide useful guidelines appropriate adjustments in the dosage depending on the needs of an individual patient factoring in disease, gender, performance status, age and other general health conditions will be made at the time of administration to a patient by a trained physician. The same is true for means of administration, routes of administration as well.

To monitor disease course and evaluate the cancer cell killing it is contemplated that the patients should be examined for appropriate tests every month. To assess the effectiveness of the drug, the physician will determine parameters to be monitored depending on the type of cancer/tumor and will involve methods to monitor reduction in tumor mass by for example computer tomography (CT) scans, PET scans, gallium scans, detection of the presence of the CD26 antigen on cell surface and in serum, and in some cases the additional detection of other tumor markers such as PSA (prostrate specific antigen) in prostrate cancer, HCG in germ tumor, CEA in colon cancer, CA125 in ovarian cancer, LDH and B2 microglobulin in lymphomas, and the like. Tests that will be used to monitor the progress of the patients and the effectiveness of the treatments include: physical exam, X-ray, blood work, bone marrow work and other clinical laboratory methodologies. The doses given in the phase 1 study will be escalated as is done in standard phase 1 clinical phase trials, i.e. doses will be escalated until maximal tolerable ranges are reached.

Clinical responses may be defined by acceptable measure. For example, a complete response may be defined by complete disappearance of the cancer cells whereas a partial response may be defined by a 50% reduction of cancer cells or tumor mass.

The typical course of treatment will vary depending upon the individual patient and disease being treated in ways known to those of skill in the art. For example, a patient with T-cell lymphoma might be treated in four week cycles. The duration of treatment will similarly be varied, although potentially longer duration may be used if no adverse effects are observed with the patient, and shorter terms of treatment may result if the patient does not respond or suffers from intolerable toxicity.

All of the compositions and/or methods disclosed and claimed herein can be made and executed without undue experimentation in light of the present disclosure. while the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,340,535
U.S. Pat. No. 4,366,241
U.S. Pat. No. 4,472,509
U.S. Pat. No. 4,676,980
U.S. Pat. No. 4,816,567
U.S. Pat. No. 4,867,973
U.S. Pat. No. 5,021,236
U.S. Pat. No. 5,120,642
U.S. Pat. No. 5,565,332
U.S. Pat. No. 5,693,762
U.S. Pat. No. 6,218,372
U.S. Pat. No. 6,218,372
Abbondanzo, *Ann Diagn Pathol*, 3(5):318-327, 1990.
Allred et al., *Arch Surg*, 125(1):107-13, 1990.
Antibodies: A Laboratory Manual, Cold Spring Harbor Laboratory, 1988
Asada et al., *Histopathol.*, 23:265-270, 1993.
Ashwani et al., *J Immunol.* 165:1882-1888, 2000.
Bacigalupo et al., *Acta haematol.* 73:185-186, 1985.
Bauvois et al., *Br. J. Cancer*, 79:1042-1048, 1999.
Boussiotis et al., *Science*, 278:124-127, 1997.

Brodeur et al., Monoclonal Antibody Production Techniques and Applications, pp. 51-63 (Marcel Dekker, Inc., New York, 1987).
Brown et al. *Immunol Ser,* 53:69-82, 1990.
Campbell et al., *J. Mol. Biol.,* 180:1-19, 1984.
Carbone et al., *Blood,* 86:4617-4626, 1995.
Carbone et al., *Human Pathol.,* 25:1360-1365, 1994.
Chen et al., *J Immunol.,* 163:5796-5805, 1999.
Cheukuri et al., *Immunity,* 2001; 14: 657-660.
Clackson et al., Nature 352, 624-628, 1991.
Dang et al., *Cell. Immunol.,* 125:42-57, 1990.
Dang et al., *J. Exp. Med.,* 172:649-652, 1990.
Dang et al., *J. Immunol.,* 144:4092-4100, 1990.
Dang et al., *J. Immunol.,* 145:3963-3971, 1990.
Dang et al., *J. Immunol.,* 147:2825-2832, 1991.
Dang et al., *J. Immunol.,* 156:1349-1355, 1996.
Datto et al., *Proc. Natl. Acad. Sci. USA,* 92:5545-5549, 1995.
De Meester et al., *Immunobiol.* 188:145-158, 1993.
De Meester et al., *Immunobiol.,* 188:145-158, 1993.
Dong et al., *Mol. Immunol.,* 35:13-21, 1998.
Eguchi et al., *J. Immunol.,* 142:4233-4240, 1989.
Eguchi et al., *J. Immunol.,* 142:4233-4240, 1989.
El-Deiry et al., *Cancer Res.,* 54:1169-1174, 1994.
El-Deiry et al., *Cell,* 75:817-825, 1993.
EP 03089
Falcioni et al., *Human Immunol.,* 50:79-90, 1996.
Fischer et al., *Blood,* 72:234-240, 1988.
Fleischer, *J. Immunol.,* 138:1346-1350, 1987.
Fox et al., *J. Immunol.,* 133: 1250-1256, 1984.
Gefter et al., *Somatic Cell Genet,* 3(2):231-6, 1977.
Gerli et al., *Clin. Immunol. Immunopathol.,* 80:31-37, 1996.
Ghosh and Bachhawat, In: *Liver Diseases, Targeted Diagnosis and Therapy Using Specific Receptors and Ligands.* Wu et al., eds., Marcel Dekker, New York, pp. 87-104, 1991.
Goding, Monoclonal Antibodies: Principles and Practice, pp. 59-103 Academic Press, 1986.
Griffith et al., *EMBO J.,* 12:725-734, 1993.
Hafler et al., *J. Experi. Med,* 167:1313-1322, 1988.
Hafler et al., *N Engl J Med.,* 312: 1405-1411, 1985.
Hafler et al., *N. Engl. J. Med,* 312:1405-1411, 1985.
Hansen et al., *J. Immunol. Methods,* 119:203-210, 1989.
Hegen et al., *Immunology,* 90:257-264, 1997.
Ishii et al., *Proc Natl. Acad. Sci USA,* 98:12138-12143, 2001.
Jakobovits et al., Nature 362, 255-258, 1993.
Jakobovits et al., *Proc. Natl. Acad. Sci. USA,* 90:2551-255, 1993.
Janes et al., *J Cell Biol.* 147: 447-461, 1999.
Johnson et al., *Current Opinion in Structural Biology,* 3:564-571, 1993,
Jones et al., *Nature,* 321:522-525, 1986.
Kahne et al., *Cell. Immunol.,* 189:60-66, 1998.
Kameoka et al., *Science,* 261:466-469, 1993.
Kohler and Milstein, *Eur. J. Immunol.,* 6:511-519, 1976.
Kohler and Milstein, *Nature,* 256:495-497, 1975.
Korom et al., *Transplantation,* 63:1495-1500, 1997.
Kozbor, *J. Immunol.* 133, 3001, 1984.
Kubota et al., *Clin. Exp. Immunol.,* 89:192-197, 1992.
Kung et al., *Science.,* 206:347-349, 1979.
Lehaman et al., *Eur J Immunol.* 19:1071-1077, 1989.
Leo and Schraven, *Curr Opn Immunol.* 13:307-316, 2001.
Marks et al., *Bio/Technol.* 10, 779-783, 1992.
Marks et al., *J. Mol. Biol.* 222, 581-597, 1991.
Mattern et al., *Immunobiol.,* 188:36-50, 1993.
McCafferty et al., *Nature* 348, 552-553 [1990]
Millstein and Cuello, *Nature* 305, 537-539 (1983).
Mizokami et al., *J Rheumatol.* 23:2022-2026, 1996.
Mizokami et al., *J. Rheumatol.,* 23:2022-2026, 1996.
Morimoto and Schlossman, *Immunol. Rev.,* 161:55-70, 1998.
Morimoto et al., *Immunol Rev.* 161:55-70, 1998.
Morimoto et al., *J. Immunol.,* 143:3430-3439, 1989.
Morimoto et al., *J Immunol.,* 134: 3762-3769, 1985.
Morrison et al., *J. Exp. Med.,* 177:1135-1143, 1993.
Morton et al., *Cancer,* 71:3737-3743, 1993.
Nakamura et al., In: *Handbook of Experimental Immunology* (4th Ed.), Weir et al., (eds). 1:27, Blackwell Scientific Publ., Oxford, 1987.
Nourse et al., *Nature.* 372:570-573, 1994.
Oravecz et al., *J. Exp. Med.,* 186:1865-1872, 1997. PCT Application WO 91/00360 PCT Application WO 92/200373 PCT Application WO 93/08829
Proost et al., *J Biol. Chem.* 273:7222-7227, 1998.
Proost et al., *J. Biol. Chem.,* 273:7222-7227, 1998.
Ravindranath and Morton, *Intern. Rev. Immunol.,* 7: 303-329, 1991.
Remington's Pharmaceutical Sciences" 15th Edition, pages 1035-1038 and 1570-1580, 1980.
Riechmann et al., *Nature,* 332, 323-327, 1988.
Rosenberg et al., *Ann Surg.* 210(4):474-548, 1989
Rosenberg et al., *N. Engl. J. Med.,* 319:1676, 1988.
Sabzevari et al., *Eur J Immunol* 27:1901-1910, 1997.
Sewing et al., *Mol Cell Biol.* 17: 5588-5597, 1997.
Sugita et al., *J Immunol,* 149: 3208-3216, 1992.
Suresh et al., *Methods in Enzymology* 121, 210, 1986.
Tanaka et al., *Int. J. Cancer,* 64:326-331, 1995.
Tanaka et al., *Journal of Immunology,* 149:481-486, 1992.
Tanaka et al., *Proc. Natl. Acad. Sci. USA,* 90:4586-4590, 1993.
Tian et al., *Cancer Res.,* 55:5335-5341, 1995.
Torimoto et al., *J. Immunol.,* 147:2514-2517, 1991.
Torimoto et al., *Mol. Immunol.,* 29:183-192, 1992.
Traunecker et al., *EMBO* 10, 3655-3659, 1991.
Verhoeyen et al., Science 239, 1534-1536, 1988.
von Bonin et al., *Immunol Rev.* 161:43-53, 1998.
von Bonin et al., *Immunol. Rev.,* 161:43-53, 1998.
Waga et al., *Nature,* 369:574-578, 1994.
Waterhouse et al., Nucl. Acids Res. 21, 2265-2266 (1993)
Wesley et al., *J. Exp. Med.,* 190:311-322, 1999.
Xiong et al., *Nature,* 366:701-704, 1993.
Yang and Kornbluth, *Trends Cell Biol.,* 9:207-210, 1999.

What is claimed is:

1. A method of treating a patient having a cancer that expresses CD26 comprising administering to said patient a pharmaceutical formulation comprising an anti-CD26 monoclonal antibody, whereby the anti-CD26 monoclonal antibody binds CD26 and arrests cell cycle, and wherein the cancer is a T-cell cancer, a B-cell cancer, a thyroid cancer, a lung adenocarcinoma, a prostate cancer, a stomach cancer, a testicular cancer, a uterine cancer, a brain cancer, a bone cancer, a rectal cancer, or a sarcoma.

2. The method of claim 1, further comprising detecting cell cycle arrest.

3. The method according to claim 1, wherein the monoclonal antibody is humanized.

4. The method of claim 1, wherein the anti-CD26 antibody is an unconjugated antibody.

5. The method of claim 1, wherein the anti-CD26 antibody is conjugated to a chemotherapeutic agent, a radionuclide, an imaging agent, a toxin, a biological agent, an enzyme inhibitor, or a second antibody.

6. The method of claim 5, wherein the enzyme inhibitor is an adenosine deaminase inhibitor, or a dipeptidyl peptidase IV inhibitor.

7. The method of claim 1, wherein the cancer is a T-cell cancer.

8. The method of claim 7, wherein the T-cell cancer is a T-cell lymphoma or a T-cell leukemia.

9. The method of claim 1, wherein the cancer is a B-cell cancer.

10. The method of claim 1, further comprising treating the patient with a second agent, wherein the second agent is a therapeutic polypeptide, a nucleic acid encoding a therapeutic polypeptide, a chemotherapeutic agent, an immunotherapeutic agent, a radiotherapeutic agent, a cytokine, a chemokine, an activating agent, or a biological response modifier.

11. The method of claim 10, wherein the second agent is administered simultaneously with the anti-CD26 antibody.

12. The method of claim 10, wherein the second agent is administered at a different time than the anti-CD26 antibody.

13. The method of claim 1, wherein the cancer is characterized by tumor formation in said patient.

14. The method of claim 1, wherein the administering is intravenous, intraarterial, intraperitoneal, intradermal, intratumoral, intramuscular, subcutaneous, intraarthricular, intrathecal, oral, dermal, nasal, buccal, rectal, or vaginal.

15. The method of claim 8, wherein the T-cell cancer is a T-cell leukemia.

16. The method of claim 15, wherein the T-cell leukemia is acute lymphoblastic leukemia, a T-cell chronic lymphocytic leukemia, a HTLV-related T-cell leukemia, or an adult T-cell leukemia.

17. The method of claim 8, wherein the T-cell cancer is a T-cell lymphoma.

18. The method of claim 17, wherein the T-cell lymphoma is a lymphoblastic lymphoma, a T-cell CD30+ anaplastic large cell lymphoma, a peripheral T-cell lymphoma, an angio-immunoblastic T-cell lymphoma, or an angiocentric T-cell lymphoma.

19. The method of claim 9, wherein the B-cell cancer is a B-cell leukemia or a B-cell lymphoma.

20. The method of claim 19, wherein the B-cell cancer is a B-cell leukemia.

21. The method of claim 20, wherein the B-cell leukemia is B-cell chronic lymphocytic leukemia.

22. The method of claim 19, wherein the B-cell cancer is a B-cell lymphoma.

23. The method of claim 1, wherein the cancer is a thyroid cancer.

24. The method of claim 1, wherein the cancer is a lung adenocarcinoma.

25. The method of claim 1, wherein the cancer is a prostate cancer.

26. The method of claim 1, wherein the cancer is a stomach cancer.

27. The method of claim 1, wherein the cancer is a testicular cancer.

28. The method of claim 1, wherein the cancer is a uterine cancer.

29. The method of claim 1, wherein the cancer is a brain cancer.

30. The method of claim 1, wherein the cancer is a bone cancer.

31. The method of claim 1, wherein the cancer is a rectal cancer.

32. The method of claim 1, wherein the cancer is a sarcoma.

* * * * *

UNITED STATES PATENT AND TRADEMARK OFFICE
CERTIFICATE OF CORRECTION

PATENT NO. : 7,658,923 B2
APPLICATION NO. : 11/676164
DATED : February 9, 2010
INVENTOR(S) : Nam Hoang Dang et al.

It is certified that error appears in the above-identified patent and that said Letters Patent is hereby corrected as shown below:

In title page, item (63) Related U.S. Application Data, insert
--Continuation of application No. 10/143,553, filed on May 10, 2002, now Patent No. 7,198,788--.

In title page, item (60) Related U.S. Application Data, insert
--Provisional application No. 60/290,531, filed on May 11, 2001--.

Signed and Sealed this

Eighteenth Day of May, 2010

David J. Kappos
*Director of the United States Patent and Trademark Office*